US 11,659,657 B2

(12) United States Patent
Viberg et al.

(10) Patent No.: US 11,659,657 B2
(45) Date of Patent: *May 23, 2023

(54) FLEXIBLE CIRCUIT PACKAGE

(71) Applicant: ORPYX MEDICAL TECHNOLOGIES INC., Calgary (CA)

(72) Inventors: David Allan Viberg, Calgary (CA); Travis Michael Stevens, Calgary (CA); Kraig Elbert Nielsen, Calgary (CA); Michael Todd Purdy, Calgary (CA)

(73) Assignee: ORPYX MEDICAL TECHNOLOGIES INC., Calgary (CA)

( * ) Notice: Subject to any disclaimer, the term of this patent is extended or adjusted under 35 U.S.C. 154(b) by 155 days.

This patent is subject to a terminal disclaimer.

(21) Appl. No.: 17/241,162

(22) Filed: Apr. 27, 2021

(65) Prior Publication Data

US 2021/0251073 A1 Aug. 12, 2021

Related U.S. Application Data

(63) Continuation of application No. 16/614,816, filed as application No. PCT/CA2018/050618 on May 25, 2018, now Pat. No. 11,026,325.

(60) Provisional application No. 62/511,142, filed on May 25, 2017.

(51) Int. Cl.
*G01L 1/00* (2006.01)
*H05K 1/02* (2006.01)
(Continued)

(52) U.S. Cl.
CPC .......... *H05K 1/0296* (2013.01); *G01K 1/026* (2013.01); *G01K 7/00* (2013.01); *G01L 1/146* (2013.01);
(Continued)

(58) Field of Classification Search
CPC .. H05K 1/0296; H05K 1/0272; H05K 1/0281; H05K 2201/09227;
(Continued)

(56) References Cited

U.S. PATENT DOCUMENTS 4,448,080 A * 5/1984 Dressel .................. G01N 19/08
73/40
6,462,414 B1 10/2002 Anderson
(Continued)

FOREIGN PATENT DOCUMENTS

CA 2912586 A1 11/2014
CN 102569209 A 7/2012
(Continued)

OTHER PUBLICATIONS

Extended European Search Report issued in European patent application No. 18805979.4 dated Feb. 4, 2021.
(Continued)

*Primary Examiner* — Max H Noori
(74) *Attorney, Agent, or Firm* — ABM Intellectual Property Inc.; Adrienne Bieber McNeil

(57) ABSTRACT

A flexible circuit package. The circuit package includes a termination point on a flexible base substrate. The termination point is connected with an interface by conductive material on the base substrate. The conductive material extends across the surface area of the base substrate in multiple individual connections, which are in communication with each other and separated by voids in the conductive material for mitigating communication failure between the termination point and the interface during or following flexion, stretching, compression or other deformation of the base substrate and the circuit package. The termination point may include an input module such as a sensor, switch or other input. The termination point may include an output
(Continued)

module such as a light, vibrator or other output. The interface may include an output interface for receiving data or an input interface for sending a command or other signal.

20 Claims, 18 Drawing Sheets

(51) Int. Cl.
  *G01K 1/02* (2021.01)
  *G01K 7/00* (2006.01)
  *G01L 1/14* (2006.01)

(52) U.S. Cl.
  CPC ......... *H05K 1/0272* (2013.01); *H05K 1/0281* (2013.01); *H05K 2201/0979* (2013.01); *H05K 2201/09227* (2013.01); *H05K 2201/10151* (2013.01)

(58) Field of Classification Search
  CPC . H05K 2201/0979; H05K 2201/10151; G01K 1/026; G01K 7/00; G01L 1/146
  See application file for complete search history.

(56) References Cited

U.S. PATENT DOCUMENTS

| | | | |
|---|---|---|---|
| 6,829,942 B2 | 12/2004 | Yanai et al. | |
| 9,041,205 B2 | 5/2015 | Karhade et al. | |
| 9,544,994 B2 * | 1/2017 | Kwon | H01L 27/3276 |
| 10,041,855 B2 * | 8/2018 | Nino | G01N 19/08 |
| 11,026,325 B2 * | 6/2021 | Viberg | G01L 1/26 |
| 2005/0208781 A1 | 9/2005 | Fitzsimmons et al. | |
| 2005/0280157 A1 | 12/2005 | Roush et al. | |
| 2007/0134473 A1 | 6/2007 | Kim | |
| 2008/0237787 A1 | 10/2008 | Yonezu et al. | |
| 2009/0001531 A1 | 1/2009 | Do et al. | |
| 2009/0224395 A1 | 9/2009 | Fan | |
| 2013/0213144 A1 | 8/2013 | Rice et al. | |
| 2014/0254121 A1 | 9/2014 | Jung et al. | |
| 2016/0348223 A1 * | 12/2016 | Groth | B23P 6/04 |
| 2017/0077147 A1 | 3/2017 | Kwon et al. | |
| 2020/0203641 A1 | 6/2020 | Lee et al. | |

FOREIGN PATENT DOCUMENTS

| | | |
|---|---|---|
| CN | 206864451 U | 1/2018 |
| JP | 60124056 | 8/1985 |
| JP | 2008504673 A | 2/2008 |
| JP | 2015513422 A | 5/2015 |
| WO | 2016070078 A1 | 5/2016 |

OTHER PUBLICATIONS

International Search Report & Written Opinion of the International Searching Authority in PCT/CA/050618, dated Nov. 29, 2018.
Office Action dated May 25, 2022 in Japanese patent application No. 2019-565413, with English translation.

* cited by examiner

FLEXIBLE CIRCUIT PACKAGE

CROSS REFERENCE TO RELATED APPLICATIONS

This application is a continuation of U.S. patent application Ser. No. 16/614,816, which is a national stage entry of International Patent Application No. PCT/CA2018/050618 filed on May 25, 2018, which claims the benefit of U.S. Provisional Patent Application No. 62/511,142 on filed May 25, 2017. Each of the aforementioned patent applications is incorporated herein by reference in its entirety.

FIELD

The present disclosure relates to a flexible circuit package.

BACKGROUND

Flexible circuitry may be used in applications requiring the circuitry to be placed in a multitude of potentially non-planar environments. One application of flexible circuitry is for a pressure sensor for measurement of pressure on an individual, for example in a hospital mattress for measuring movement and in car seats for determining the presence of a passenger. Flexible circuits may break within circuit traces or the sensors themselves, compromising or eliminating sensor or other functions.

Pressure measurement packages may include several sheets with electrodes and pressure-sensitive materials printed onto the sheets. The sheets may be flexible, allowing for some degree of bending and stretching. However, many conductive materials are not inherently flexible. Some conductive inks provide flexible options, but many such inks lack the electrical characteristics as more traditional conductors. For example, many such inks have higher resistances, which may introduce error in pressure-measurement applications. Traditionally conductive material, such as metal, may break during bending and flexion of the sheet onto which it is printed. This may cause electrical discontinuity and overall breakage of the circuit traces and the sensors.

U.S. Pat. No. 6,829,942 describes a package including a reinforcement sheet underneath a base sheet. The reinforcement sheet may limit over-flexion of the base sheet, potentially mitigating trace breakage. However, the reinforcement sheet also limits the flexibility of the base sheet.

It is, therefore, desirable to provide a flexible circuit package with reliable, durable, and consistent electrical integrity, while maintaining flexibility.

SUMMARY

It is an object of the present disclosure to obviate or mitigate at least one disadvantage of previous flexible circuit packages. Herein provided is a flexible circuit package including features for mitigating loss of electrical communication during or as a result of flexion of the package during use. The electrical communication may be with an input module (e.g. a sensor, switch etc.), an output module (a light, speaker, transmission device, wired data connection, etc.) or any suitable termination point.

The circuit package includes a flexible base substrate. A termination point may be deposited on or otherwise connected with the base substrate. The termination point may include an input module for receiving an input of stimulus and communicating the input to an output interface for connecting to an external processor. The termination point may include an output module for receiving a command or other signal from an input interface, and sending a signal, carrying out a process or otherwise changing state based on the command or signal. The input module or output module may detect, or be actuated by, changes in an electrical property, of material in the sensor (e.g. resistance, capacitance, conductance, inductance, etc.).

A conductive material may be deposited on or otherwise connected with the base substrate for providing electrical communication between the termination point and the interface, which may include communication between the input module and the output interface, communication between the output module and the input interface, or both. The conductive material is deposited on or otherwise connected with the base substrate in an interconnected pattern with multiple connection points between individual leads. The multiple connections define multiple void spaces, providing a patterned interconnect between the termination point and the output interface or input interface.

The individual lead lines and resulting void spaces are positioned on the base substrate patterned with lead lines in directions selected for, and intersecting at angles for, acting as rip-stops, providing stoppage points to mitigate propagation of cracks through the conductive material. Interconnected leads may be arranged in an orthogonal grid, a hexagonal grid, other grid, an offset pattern or otherwise. The multiple individual leads of the conductive material and the corresponding voids defined in the conductive material may be located over a surface area of the base substrate for providing redundant electrical communication pathways. The redundancy may mitigate negative effects on signal communication resulting from cracking of the conductive material during bending.

In a first aspect, herein provided is a flexible sensor package. The package includes at least two electrodes on a flexible base substrate. The electrodes are physically separated and electrically isolated from each other in a resting state of the package. When force is applied to the package, the electrodes are forced into electrical communication with each other, completing a circuit. At least one of the electrodes is in electrical communication with an output from the package by a conductive material that may be located over a surface area of the base substrate with voids defined in the conductive material for providing redundant electrical communication pathways between the sensor and the output interface for mitigating electrical failure of a circuit including the electrodes under or following flexion, stretching, compression or other deformation of the base substrate and the package.

In another aspect, herein provided is a flexible force-sensitive circuit package including features for mitigating loss of electrical communication with an electrode during or as a result of flexion of the package. The package may include a base substrate with two layers. A first electrode may be deposited on or otherwise connected with a first layer of the base substrate. A second electrode may be deposited on or otherwise connected with a second layer of the base substrate and positioned relative to the first electrode such that portions of the first electrode are aligned with portions of the second electrode. The first and second layers of the base substrate may be separated by a spacer, introducing a gap between the first and second layers of the base substrates and forming a chamber. The first and second electrodes face each other and into the chamber. Together, the first and second electrodes, the spacer, and the chamber define a force-sensitive area, which may be applied as a pressure sensor, a pressure-based actuator, or for other uses. The force-sensitive area is in communication with an output interface for receiving an input of force and communicating data of the input to an output interface for connecting to an external processor. A conductive material may be deposited on or otherwise connected with the base substrate for providing electrical communication between the electrodes and the output interface. The conductive material may be located over a surface area of the base substrate with voids defined in the conductive material for providing redundant electrical communication pathways between the force-sensitive area and the output interface. The redundancy may mitigate the negative effects on signal communication that may result from cracking of the conductive material during bending.

In some embodiments, the electrodes may each be manufactured using a variety of conductive layers and conductive materials. For example, a capacitor may be formed by layering electrodes between base layers, the electrode at least partially overlapping with one another. A dielectric compressible spacer patterned between the electrode such that open gaps between the electrode are created, providing a capacitive sensor. When the sensor package is compressed, the electrodes would be closer to one another through the dielectric compressible spacer between the electrodes, resulting in a measurable change in the capacitance. The sensor may measure changes in an electrical property, with examples of the electrical property including resistance, capacitance, conductance, inductance, or a combination thereof, of the electrodes. In some embodiments, the electrodes in the capacitor may include plates on either side of the dielectric compressible spacer.

In some embodiments, reinforcement elements may be connected with the base substrate in alignment with potentially vulnerable points, which may include the pressure-sensing areas, areas of the conductive material that cross portions of the package likely to be subject to high flexion, or any other suitable area. The reinforcement elements redistribute forces to mitigate permanent and non-permanent deformation of specific areas of the package and underlying conductive layers, in this case, the electrodes and conductive materials.

In some embodiments, a fluid channel may be implemented within the spacer for allowing airflow from the chamber. An internal fluid reservoir may be included within the package in communication with the fluid channels for providing airflow without communication externally to the package.

In a first aspect, herein provided is a flexible circuit package. The circuit package includes a termination point on a flexible base substrate. The termination point is connected with an interface by conductive material on the base substrate. The conductive material extends across the surface area of the base substrate in multiple individual connections, which are in communication with each other and separated by voids in the conductive material for mitigating communication failure between the termination point and the interface during or following flexion, stretching, compression or other deformation of the base substrate and the circuit package. The termination point may include an input module such as a sensor, switch or other input. The termination point may include an output module such as a light, vibrator or other output. The interface may include an output interface for receiving data or an input interface for sending a command or other signal.

In a further aspect, herein provided is a circuit package including a flexible base, a termination point connected with the base, an interface for communicating with the termination point through the circuit package, and conductive material connected with the base substrate, and in communication with the termination point and with the interface for providing communication between the termination point and the interface. At least a first portion of the conductive material includes a first interconnect including at least two leads of the conductive material, the two leads separated by a void for mitigating propagation of a crack in the conductive material.

In some embodiments, the termination point includes an input module for receiving data and the interface includes an output interface for providing the data externally to the circuit package.

In some embodiments, the input module includes a sensor and the data includes data of a stimulus on the sensor.

In some embodiments, the sensor includes a force-sensitive area and the stimulus includes application of a force to the force-sensitive area.

In some embodiments, the force-sensitive area includes an electrode having an electrical property that is variable in response to the force.

In some embodiments, the force-sensitive area includes a first electrode connected with the base substrate, the first electrode including a first sensor portion in electrical communication with the conductive material, and a second electrode connected with the base substrate, the second electrode including a second sensor portion in electrical communication with the conductive material. The first electrode is positioned relative to the second electrode to be in electrical isolation from the second electrode in the absence of the force and to be urged into contact with the second electrode when the force is applied to the force-sensitive area.

In some embodiments, the force-sensitive area includes a conductor bridge connected with the base substrate for providing electrical communication between the first electrode and the second electrode when the force is applied to the force-sensitive area.

In some embodiments, the base substrate includes a first base substrate layer connected with a second base substrate layer, the first electrode is connected with the first base substrate layer, the second electrode is connected with the first base substrate layer, the force-sensitive area includes a conductor bridge connected with the second base substrate layer, and the conductor bridge is positioned on the second substrate layer relative to the first electrode and the second electrode for providing electrical communication between the first electrode and the second electrode when the force is applied to the force-sensitive area.

In some embodiments, the base substrate includes a first base substrate layer connected with a second base substrate layer, the first electrode is connected with the first base substrate layer, the second electrode is connected with the second base substrate layer, the force-sensitive area includes a conductor bridge positioned between the first base substrate layer and the second base substrate layer, and the conductor bridge is positioned between the first base substrate layer and the second base substrate layer relative to the first electrode and the second electrode for providing electrical communication between the first electrode and the second electrode when the force is applied to the force-sensitive area.

In some embodiments, the base substrate includes a first base substrate layer connected with a second base substrate layer, a spacer is located between the first substrate layer and the second substrate layer for defining a chamber between the first substrate layer and the second substrate layer, the first electrode is connected with the first base substrate layer, the second electrode is connected with the first base substrate layer, and the conductor bridge is connected with the spacer and positioned within the chamber and intermediate the first electrode and the second electrode, for providing electrical communication between the first electrode and the second electrode when the force is applied to the force-sensitive area.

In some embodiments, the first portion of the conductive material extends between the first sensor portion and the output interface.

In some embodiments, a second portion of the conductive material includes a second interconnect including at least two leads of the conductive material, the two leads separated by a void, and the second portion of the conductive material extends between the second sensor portion and the output interface.

In some embodiments, the base substrate includes a first base substrate layer connected with a second base substrate layer, the first electrode is connected with the first base substrate layer, the second electrode is connected with the second base substrate layer, a spacer is located between the first substrate layer and the second substrate layer for defining a chamber between the first substrate layer and the second substrate layer, and the first electrode and the second electrode are positioned relative one another for providing electrical communication between the first electrode and the second electrode when the force is applied to the force-sensitive area.

In some embodiments, the circuit package includes a fluid channel in communication with the force-sensitive area for relief of air pressure within the base substrate when the force-sensitive area is exposed to pressure.

In some embodiments, the circuit package includes a fluid reservoir within the base substrate and in fluid communication with the fluid channel for receiving air pressure from the fluid channel.

In some embodiments, the circuit package includes an output module for changing state in response to a signal, and the interface includes an input interface for providing a signal to the output module.

In some embodiments, the termination point includes an output module for changing state in response to a signal, and the interface includes an input interface for providing a signal to the output module.

In some embodiments, the termination point includes an electrode having an electrical property that is variable in response to temperature and the stimulus includes a change in temperature.

In some embodiments, the first interconnect includes a plurality of leads of the conductive material separated by a plurality of voids for mitigating crack propagation through the conductive material.

In some embodiments, the plurality of leads of the conductive material are staggered relative to plurality of voids.

In some embodiments, the plurality of leads of the conductive material are positioned relative to the voids in an orthogonal grid, a non-orthogonal quadragonal grid, a hexagonal grid, offset voids or offset circular voids.

In some embodiments, the circuit package includes an expected axis of flexion of the circuit package.

In some embodiments, the circuit package includes a pair of relief cuts in the base substrate for locating the expected axis of flexion between the pair of relief cuts.

In some embodiments, the first interconnect is located along the expected axis of flexion.

In some embodiments, the circuit package includes an interconnected reinforcement located along the expected axis of flexion.

In some embodiments, the circuit package includes an interconnected connection point connecting the termination point with the conductive material.

In some embodiments, the circuit package includes a reinforcement element connected with the base substrate covering at least the surface area of the input module and a connection point between the termination point and the conductive material, the reinforcement element having a greater rigidity than the base substrate.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached figures, in which features sharing reference numerals with a common final three digits of a reference numeral correspond to similar features across multiple figures (e.g. the base substrate 20, 120, 220, 320, 420, 520, 620, 720, 820, 920, 1020, 1120, 1220, 1320, 1420, 1520, 1620, 1720, 1820 etc.).

DETAILED DESCRIPTION

Figure 1:
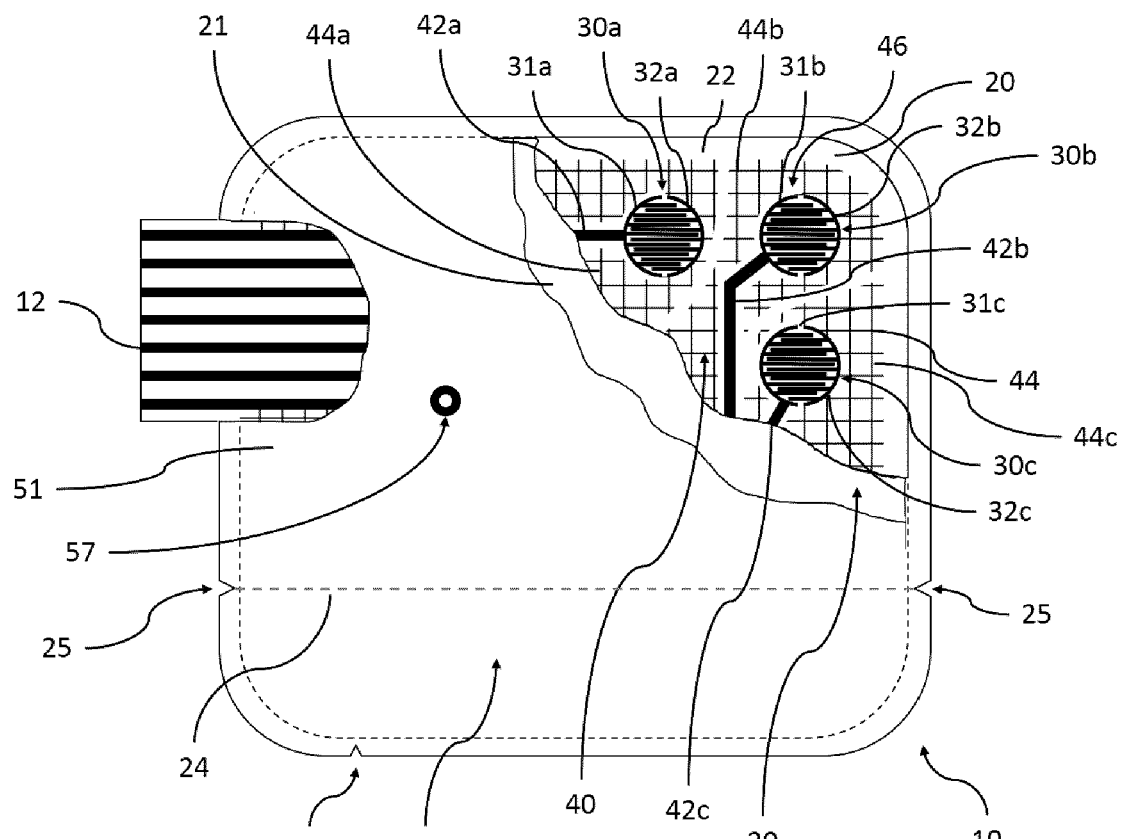
FIG. 1 is a plan view of a flexible circuit package.

Generally, the present disclosure provides a flexible circuit package. Connections between a termination point and an interface include features for mitigating damage to conductive material during or as a result of flexion of the package, and signal loss as a result of the damage. It is an object of the present disclosure to obviate or mitigate at least one disadvantage of previous flexible circuit packages. Herein provided is a flexible circuit package including features for mitigating loss of electrical communication with a termination point during or as a result of flexion of the package during use.

The termination point may include an input module (e.g. a sensor, switch etc.), an output module (a light, speaker, transmission device, wired data connection, etc.) or any suitable termination point. The interface may include an output interface for connecting to an external processor or otherwise providing data or commands externally to the flexible circuit package, an input interface for receiving an input of stimulus from a processor, user or otherwise externally from the flexible circuit package, or any suitable interface. The output module receives a command or other signal from the input interface, and sending a signal, carrying out a process or otherwise changing state based on the command or signal. The input module or output module may detect, or be actuated by, changes in an electrical property, of material in the sensor (e.g. resistance, capacitance, conductance, inductance, etc.).

The package includes a flexible base substrate. One or more termination points may be deposited on or otherwise connected with the base substrate. Functionality of the termination point may include detecting or responding to changes in an electrical property, with examples of the electrical property including resistance, capacitance, conductance, inductance, or a combination thereof, of material in the termination point.

A conductive material may be deposited on or otherwise connected with the base substrate for providing electrical communication between the termination point and the interface. The conductive material may be located over a surface area of the base substrate with voids defined in the conductive material for providing redundant electrical communication pathways between the sensor and the output interface. The redundancy may mitigate the negative effects on signal communication that may result from cracking of the conductive material during bending.

The conductive material may be positioned in an interconnected pattern with multiple lead lines intersecting at angles selected to define voids to more effectively provide rip-stops. Individual lead lines and resulting void spaces are positioned on the base substrate patterned with lead lines in directions selected for, and intersecting at angles for, acting as rip-stops, providing stoppage points to mitigate propagation of cracks through the conductive material. Interconnected leads may be arranged in an orthogonal grid, a hexagonal grid, other grid, an offset pattern, offset circular voids or otherwise. The multiple individual leads of the conductive material and the corresponding voids defined in the conductive material may be located over a surface area of the base substrate for providing redundant electrical communication pathways. The redundancy may mitigate negative effects on signal communication resulting from cracking of the conductive material during bending. As used herein "pattern" or "patterned" includes any shape in which the conductive material is located on the base material and does not require a repeating or regular pattern of the conductive material.

The termination point may include a sensor or other input module for receiving an input of stimulus and communicating data of the input to an output interface for connecting to an external processor. The sensor may detect changes in an electrical property, with examples of the electrical property including resistance, capacitance, conductance, inductance, or a combination thereof, of material in the sensor. Similarly, the termination point may include a light, a transmission device, a speaker, a vibrator or other output module that changes state in response to a signal from an input interface. Electronic devices actuated at the termination point may include measurement electronics, power or amplifier electronics, driving or sensing electrodes, selection circuitry, converters, processors, or any other electronics.

FIG. 1 is a circuit package 10. Sensors 30a, 30b and 30c are distributed across a base substrate 20, which includes a first base substrate layer 21 and a second base substrate layer 22. The base substrate 20 is manufactured from a flexible material (e.g. polyethylene terephthalate, polyimide, polyester, cotton, wool, hemp, other fabrics, etc.), and can flex, bend, and curve accordingly. Conductive material 40 is connected with the base substrate 20. The conductive material 40 may be transferred onto the base substrate 20 using any suitable method (e.g. flexible circuit board printing techniques, sputtering, etching, photolithographic techniques, weaving, etc.). A protective cover 50 is located externally to the base substrate 20 and the conductive material 40 for mitigating damage to the conductive material 40 or the base substrate 20 (e.g. punctures, scratches, etc.). The protective cover 50 includes a first protective layer 51 and a second protective layer 52 (see FIG. 5).

The conductive material 40 defines the sensors 30a, 30b and 30c. The conductive material 40 also defines connection traces 42a, 42b and 42c. The connection traces 42 connect the sensors 30a, 30b and 30c to an output interface 12 for connecting the circuit package 10 to measurement electronics. The output interface 12 may be a wired, wireless or any suitable connection. The circuit package 10 includes sensors 30a, 30b and 30c, which may include pressure sensors. Other suitable sensors may also be applied, with examples including the deformation sensors 535 of the package 510 in FIGS. 10 and 11, and the temperature sensors 837 of the package 810 in FIG. 14.

Patterned interconnects 44a, 44b and 44c are defined with void spaces 46 in between leads of the conductive material 40 for mitigating propagation of cracks in the conductive material 40 during flexion of the circuit package 10. Acting as rip-stops, the void spaces 46 provide breakpoints across the surface of the conductive material 40, slowing crack propagation and facilitating maintaining the electrical integrity of any connection including the patterned interconnects 44a, 44b and 44c during and following flexion, stretching, compression or other deformation of the circuit package 10.

Figure 2:
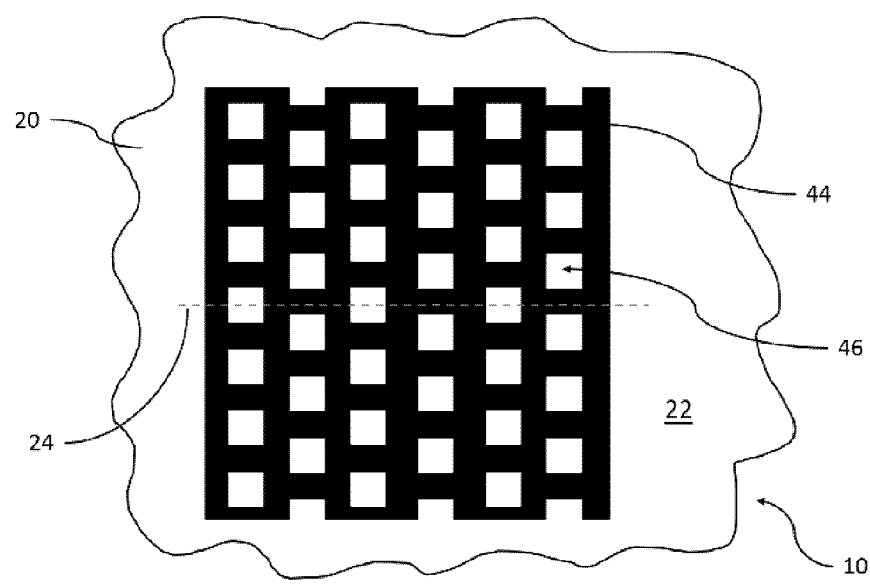
FIG. 2 is a detail view of a conductive material trace in an interconnecting pattern with offset void spaces.

FIG. 2 shows the patterned interconnects 44 in detail. As illustrated in the figures, the patterned interconnects 44 are configured in an offset grid pattern, with the void spaces 46 offset from one another, such that there are no continuous traces along an expected axis of flexion 24. The patterned interconnects 44 may be connected with the base substrate 20 in a variety of ordered patterns or randomized arrangements other than those shown in FIG. 2, with less than complete coverage of the base substrate 20. The void spaces 46 within any such pattern may be provided in a variety of shapes and sizes (e.g. orthogonal grids, non-orthogonal straight-line grids, curved grids, adjoining circles or other rounded shapes, honeycombs, etc.) to mitigate crack propagation and other damage in a given application while maintaining a selected metric of electrical performance in a connection including the patterned interconnects 44. The void spaces and the leads may be arranged in a repeating pattern, a non-repeating pattern, a random pattern, or any suitable pattern to provide multiple redundant leads between the output interface 12 and the sensors 30.

The sensors 30, the connection traces 42, and the patterned interconnects 44 may be layered in various patterns, and other features may be included, for mitigating interconnect failure and sensor failure. As used herein, the term "interconnect failure" refers to the diminishment of desirable electrical characteristics in a connection. Microfractures or partial cracking resulting in measurable difference in electrical characteristics and full cracking resulting in discontinuity of connection traces 42 or the patterned interconnects 44, are examples of interconnect failure. Similarly, sensor failure refers to a reduction of desirable electrical characteristics in the pressure sensor 30, the deformation sensors 535, or the temperature sensors 837, potentially resulting from cracking or discontinuity of the conductive material 40 making up the sensor 30.

As illustrated in the figures, the sensors 30 and the connection traces 42 may be connected with the base substrate 20 in straight-line patterns without sharp angles between sensors 30 and the connection traces 42. The lack of sharp angles may mitigate interconnect failure at connection points between the sensors 30 and the connection traces 42.

Figure 13:
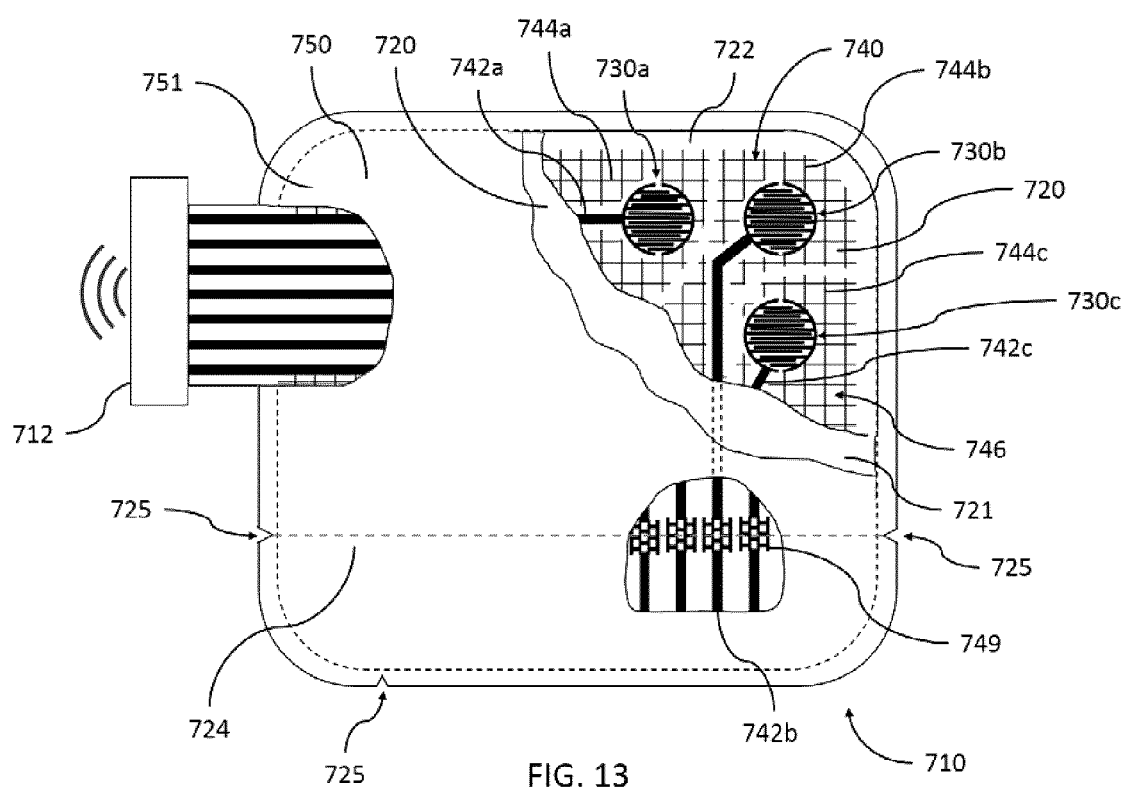
FIG. 13 is a plan view of a flexible circuit package.

To further mitigate the effects of cracks on selected portions of the conductive material 40, relief cuts 25 may be made in the base substrate 20. The relief cuts 25 provide a preferred bending axis, and redistribute the flexing forces to portions of the circuit package 10 that lack connection points between the sensors 30 and the connection traces 42. For example, the relief cuts 25 may redistribute the flexing forces along the expected axis of flexion 24 where no patterned interconnect 44 or connection trace 42 is present, or if a patterned interconnect 44 or connection trace 42 must cross the expected axis of flexion 24, that it does so perpendicularly or at an angle otherwise selected to mitigate damage to the connection trace 42 or patterned interconnect 44. The connection traces 42 may include a reinforced interconnected portion where the connection traces 42 cross an expected axis of flexion 24, an example of which is shown in FIG. 13. The base substrate 20 may include a more flexible material along the expected axis of flexion 24 defined by the relief cuts 25 than along the sensors 30 or elsewhere on the base substrate 20.

The conductive material 40 may include a variety of materials, with examples including flexible ink, piezoresistive ink, dielectrics traces, metal traces, composite materials, or a combination of the above. Portions of the sensors 30, the connection traces 42, or the patterned interconnects 44 may be prepared from the same or different conductive material 40. The conductive material 40 may be combined in any manner or printed in layers. Combinations of different examples of the conductive material 40 with selected differing electrical and mechanical characteristics may be layered on top of one another. For example, a flexible ink may be printed on top of a metal trace. In this case, bending of the base substrate 20 on which the conductive material 40 is printed may cause microfractures to appear in the metal trace, but continuity may be maintained through the flexible ink and, the conductive material 40 may maintain suitable electrical characteristics through the flexible ink despite damage to the metal trace. Reinforcing metals or other additional materials making up the conductive material 40 may increase cost or manufacturing complexity and in many cases additional reinforcing materials are added to the conductive material 40 only at selected portions of the conductive material 40, such as where greater flexion of the circuit package 10 is expected.

A first electrode 31 and a second electrode 32 may be placed directly onto the base substrate 20 in various manners. For example, the conductive material 40 may include features that allow for soldering or other attachment to the base substrate 20, for example vias 57 through the base substrate 20, exposing the conductive material 40 to the exterior surface of the circuit package 10. In FIG. 1, the first electrodes 31*a*, 31*b*, and 31*c* respectively combine with the second electrodes 32*a*, 32*b* and 32*c* to define the sensors 30*a*, 30*b* and 30*c*.

Figure 3:
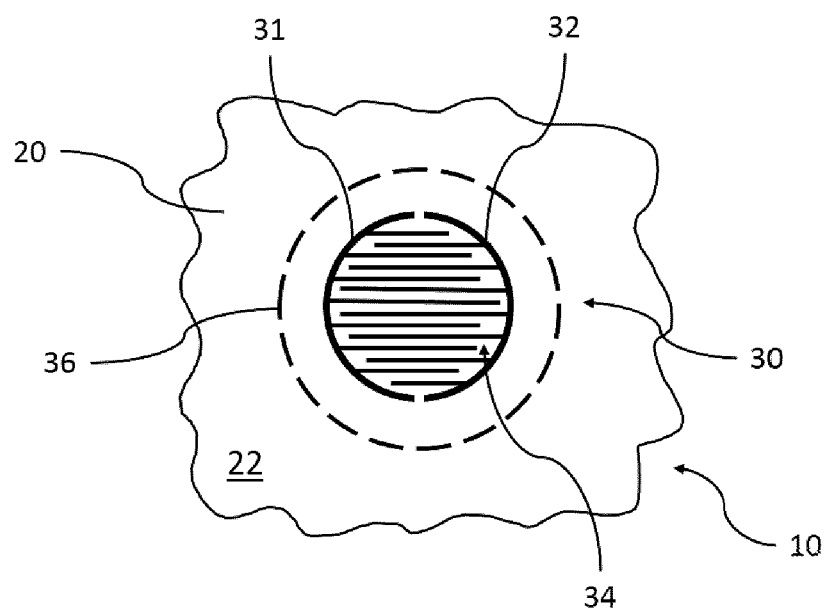
FIG. 3 is a plan view of a force-sensitive area from the package of FIG. 1.
Figure 4:
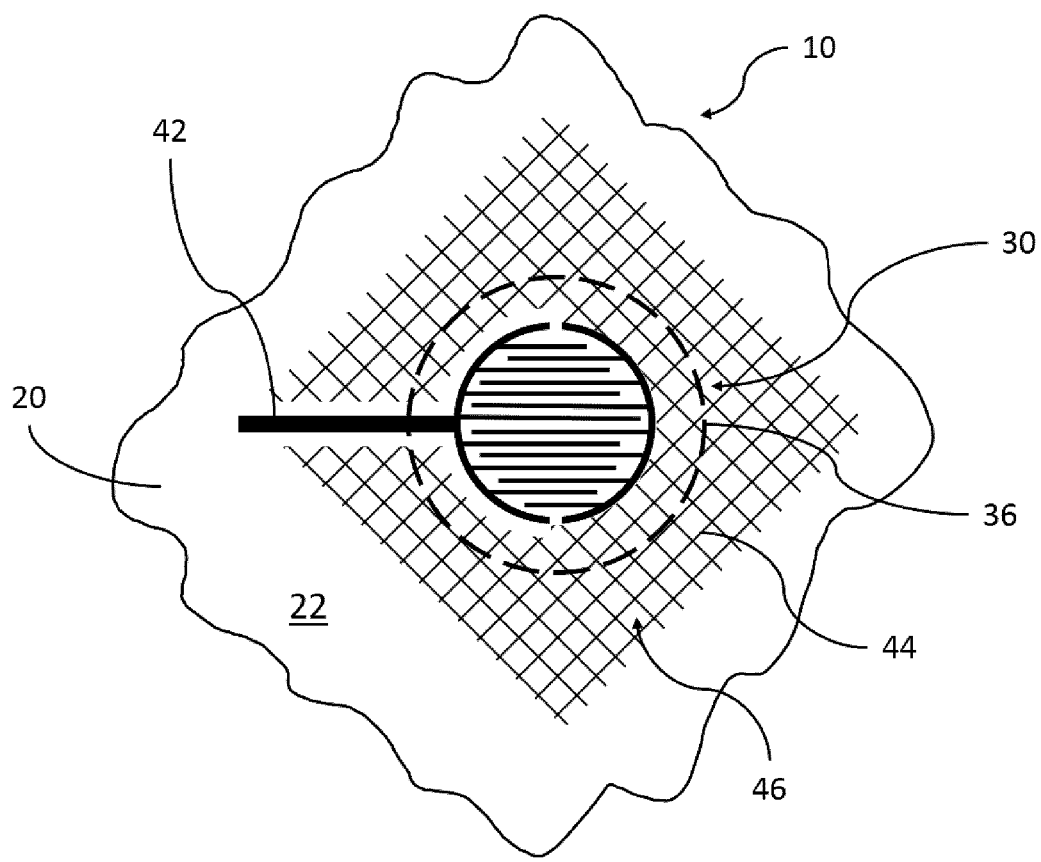
FIG. 4 is a detail view schematic of the package of FIG. 1.

FIGS. 3 and 4 show details of the sensors 30. The first electrode 31 and the second electrode 32, may be defined by the same conductive material 40 on the first base substrate layer 21. The first electrode 31, and the second electrode 32, may be configured with respect to one another in an interdigitated comb-like pattern such that the first electrode 31 and the second electrode 32 are close but not contiguous, leaving gaps 34 between the first electrode 31 and the second electrode 32, electrically isolating the first electrode 31 from the second electrode 32. The first electrode 31 and the connection trace 42 form a first circuit. The second electrode 32 and the patterned interconnect 44 form a second circuit. The first circuit is electrically isolated from its corresponding second circuit in the absence of an input of force on the pressure sensor 30.

Other shapes of first and second electrodes may be used rather than the interdigitated that fits over the underlying force-sensitive area as in FIGS. 1, 4, 6, 7 to 9, 21 and 22. For example, a ring may be used that will overlap the border of the force-sensitive area as in FIGS. 17 and 18, leaving the majority of the electrode open to applied pressures.

Figure 5:
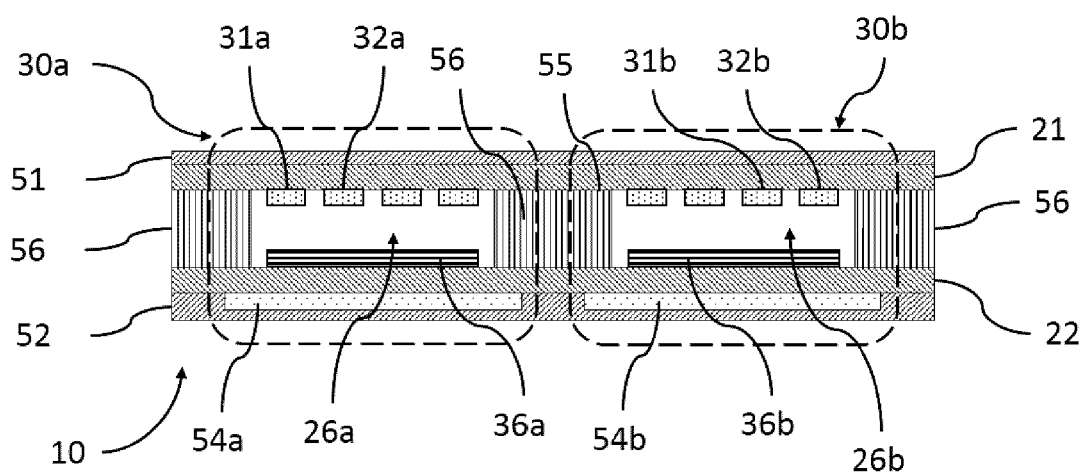
FIG. 5 is a cross-section elevation view of the package of FIG. 1.

FIG. 5 shows a cross section of the circuit package 10 showing the sensors 30*a* and 30*b*, illustrating the first base substrate layer 21 and the second base substrate layer 22. Each of the first electrode 31*a* and the connection trace 42*a*, and the first electrode 31*b* and the connection trace 42*b*, form a first circuit connected with the first base substrate layer 21. Each of the second electrode 32*a* and the patterned interconnect 44*a*, and the second electrode 32*b* and the patterned interconnect 44*b*, form a second circuit also connected with the first base substrate layer 21. Further conductive material 40 is added as conductor bridges 36*a* and 36*b* to the second base substrate layer 22. A spacer 56 is located between the first base substrate layer 21 and the second base substrate layer 22 around the footprints of the pressure sensors 30*a* and 30*b*, introducing a gap between the first base substrate layer 21 and the second base substrate layer 22, and defining a chamber 26*a* between the first electrode 31*a* and the second electrode 32*a* connected with the first base substrate layer 21, and the conductor bridge 36*a* connected with the second base substrate layer 22. Similarly, the chamber 26*b* is formed between the first electrode 31b and the second electrode 32b connected with the first base substrate layer 21, and the conductor bridge 36b connected with the second base substrate layer 22.

When pressure is applied to the circuit package 10 at the sensor 30a, the first electrode 31a and the second electrode 32a are pushed through the chamber 26a and contact the opposing conductor bridge 36a. Thus, the first electrode 31a and the second electrode 32a are brought into electrical contact with one another through the conductor bridge 36a. The greater the applied pressure, the smaller the electrical resistance between the first electrode 31a and the second electrode 32a, as larger portions of each of their respective surface areas contact the opposing conductor bridge 36a. The first electrode 31b and the second electrode 32b are similarly brought into contact with the opposing conductor bridge 36b when the sensor 30b is under pressure.

Reinforcement elements 54 may be included between the second base substrate layer 22 and the second protective layer 52. The reinforcement element 54 may further mitigate interconnect and sensor failure, by mitigating permanent and non-permanent mechanical deformation to the pressure sensor 30, conductive material 40 and base substrate 20. These reinforcement elements 54 provide areas of lower flexibility and greater rigidity, redirecting stresses applied to the circuit package 10 to areas of less fragility or importance. The reinforcement element 54 may be a stiffener material with less flexibility than the base substrate 20, and is adhered to the second base substrate layer 22. The reinforcement element 54 extends slightly beyond the border of the corresponding pressure sensor 30, ensuring full coverage of the pressure sensor 30. The reinforcement elements 54 may have a heterogeneous structure, with reinforcement materials of differing stiffness values, adhesives, and materials with other properties. The reinforcement element 54a is located between the conductor bridge 36a and the second base substrate layer 22 in the sensor 30a. The reinforcement element 54b is located between the conductor bridge 36b and the second base substrate layer 22 in the sensor 30b.

Other design or placement of reinforcement elements may be applied. For example, the reinforcement elements may include a number of interlocking discrete elements, adhered next to one another to form a semi-flexible, modular, reinforced area. For example, the reinforcement elements may contain a number of void spaces or less rigid regions, allowing for some directed bending, mitigating damage to the reinforcement elements resulting from bending. The directed bending may include bending primarily along a specified axis, for example perpendicular to interdigitated electrodes, facilitating bending of the sensor electrodes at a location that mitigates damage to the conductive material. Reinforcement elements may also be used to reinforce critical sections or the entirety of the patterned interconnects. Rather than being attached to the outside of the base substrate and positioned between a base substrate layer and a protective layer, reinforcement elements may be placed between layers of the base substrate, in predetermined locations and patterns to ensure appropriate reinforcement.

The first base substrate layer 21 and the second base substrate layer 22 are each connected with the spacers 56 by an adhesive 55. The spacer 56 and the adhesive 55 may have a unitary construction and be prepared from one material (e.g. a plastic spacer with a compatible adhesive, etc.).

Figure 6:
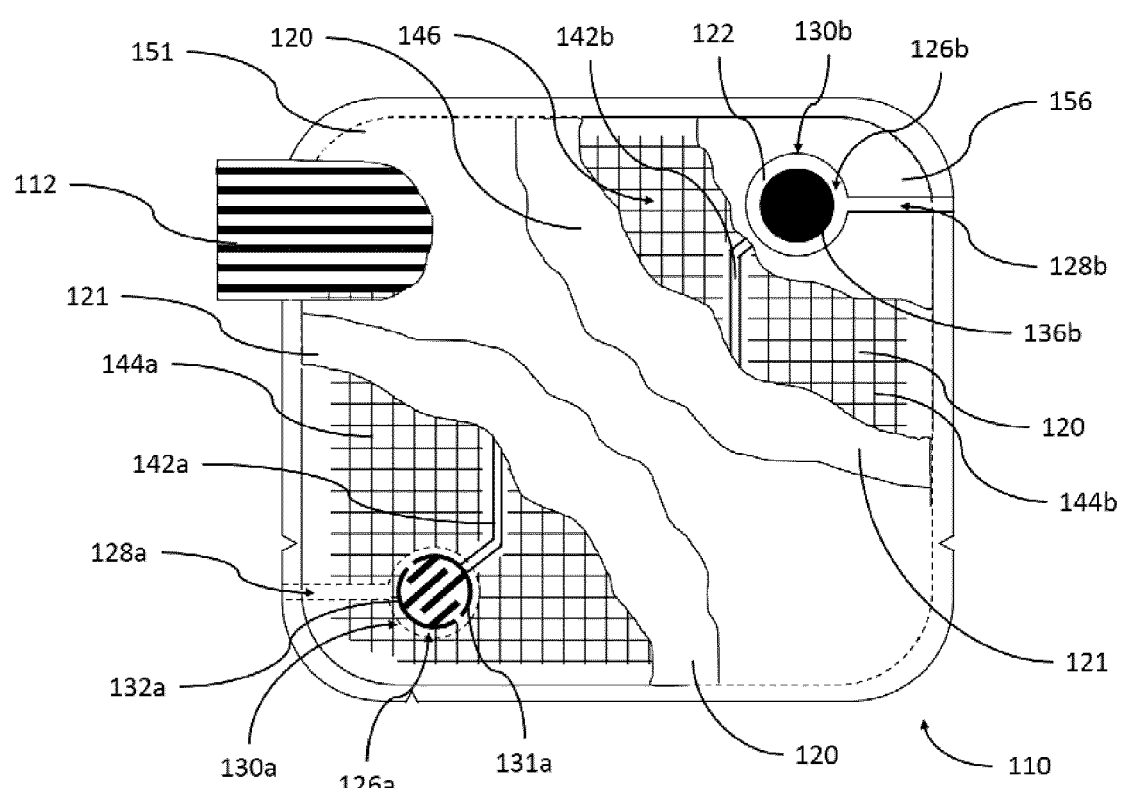
FIG. 6 is a plan view of a flexible circuit package.

FIG. 6 shows a circuit package 110. The sensor 130 is located on the base substrate 120, which includes the first base substrate layer 121 and the second base substrate layer 122. The conductive material 140 is connected with the first base substrate layer 121. The protective cover 150 is located externally to the base substrate 120 and the conductive material 140 for mitigating damage to the conductive material 140 or the base substrate 120. The protective cover 150 includes the first protective layer 151 and the second protective layer 152. The connection traces 142 connect the sensors 130 to the output interface 112 for connecting the circuit package 10 to measurement electronics. The sensors 130 may include pressure sensors but other suitable sensors may also be applied. The patterned interconnects 144 are defined with the void spaces 146 in between the leads of the conductive material 140 for mitigating propagation of cracks in the conductive material 140 during flexion of the circuit package 110. Acting as rip-stops, the void spaces 146 provide breakpoints across the surface of the conductive material 140, slowing crack propagation and facilitating maintaining the electrical integrity of any connection including the patterned interconnects 144 during and following flexion, stretching, compression or other deformation of the circuit package 110.

Fluid channels 128 are defined between the first base substrate layer 121 and the second base substrate layer 122, and within the spacers 156. The fluid channels 128 allow air to move freely within the chamber 126 during application of pressure to the sensors 130. As shown in FIG. 6, the fluid channels 128 may extend from chamber 126 to the external environment, equalizing air pressure inside the chamber 126 when pressure is applied to the sensors 130.

Figure 7:
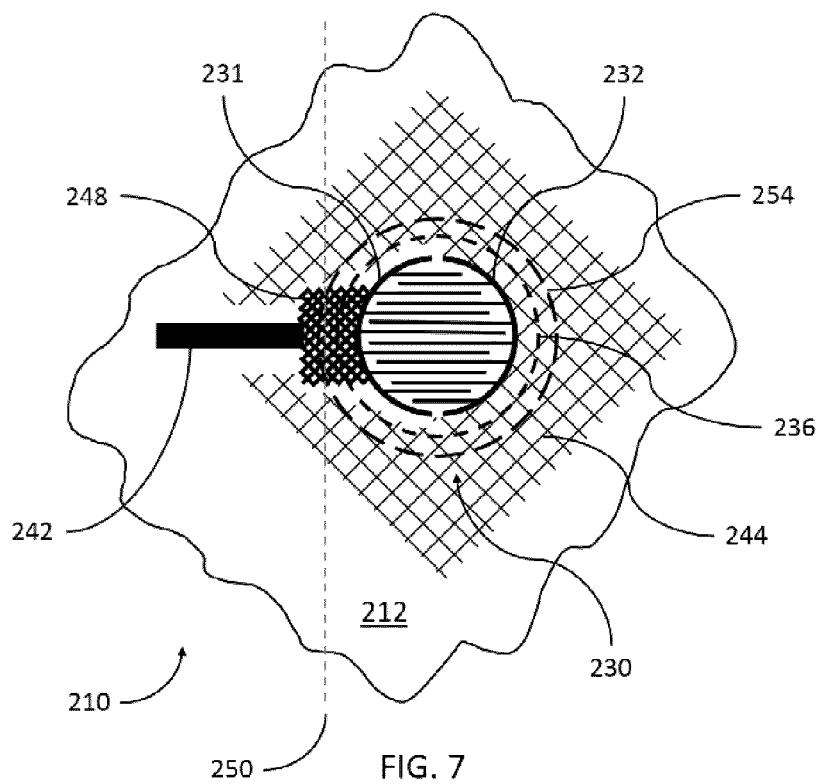
FIG. 7 is a plan view of a force-sensitive area in a flexible circuit package.

FIG. 7 shows a detail of a circuit package 210. The circuit package 210 would include the general features shown in the circuit packages 10, 110 of FIGS. 1 to 6. The sensor 230 including the first electrode 231 is connected with the connection trace 242 by an interconnected connection point 248. The interconnected connection point 248 functions similarly to the patterned interconnects 244 for the second electrode 232, and may mitigate interconnect failure within a circuit that includes the first electrode 231. The interconnected connection points 248 may facilitate maintaining continuity and electrical quality following mechanical deformation of the base substrate 212, as the void spaces in the interconnected connection points 248 provide natural stoppage points for propagating cracks. The interconnected connection point 248 may be placed at an area of high expected flexion, such as at the edge of a reinforcement element 254 or along an expected axis of flexion 250.

Figure 8:
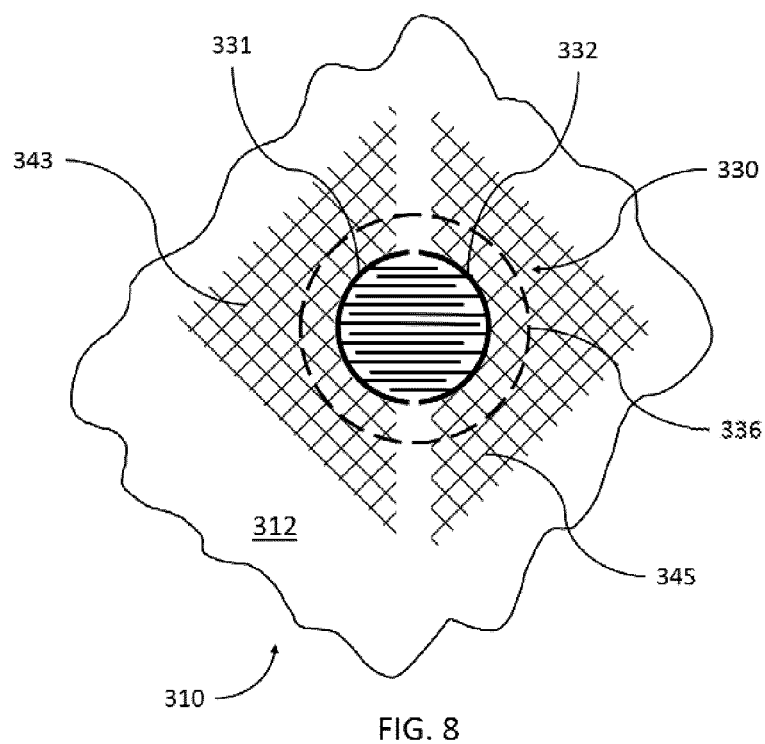
FIG. 8 is a plan view of a force-sensitive area in a flexible circuit package.

FIG. 8 shows a detail view of a circuit package 310. The circuit package 310 would include the general features shown in the circuit packages 10, 110 of FIGS. 1 to 6 other than the connection trace 42, 142. The conductive material 340 includes a first patterned interconnect 343 in electrical communication with the first electrode 331 and a second patterned interconnect 345 in electrical communication with the second electrode 332. The first patterned interconnect 343 functions similarly to the connection traces 42 of the circuit package 10 and may provide a more reliable connection for the first circuit than the connection traces 42 of the circuit package 10 for some applications where a large amount of flexion of the package 310 is expected over a large surface area near the sensor 330.

Figure 9:
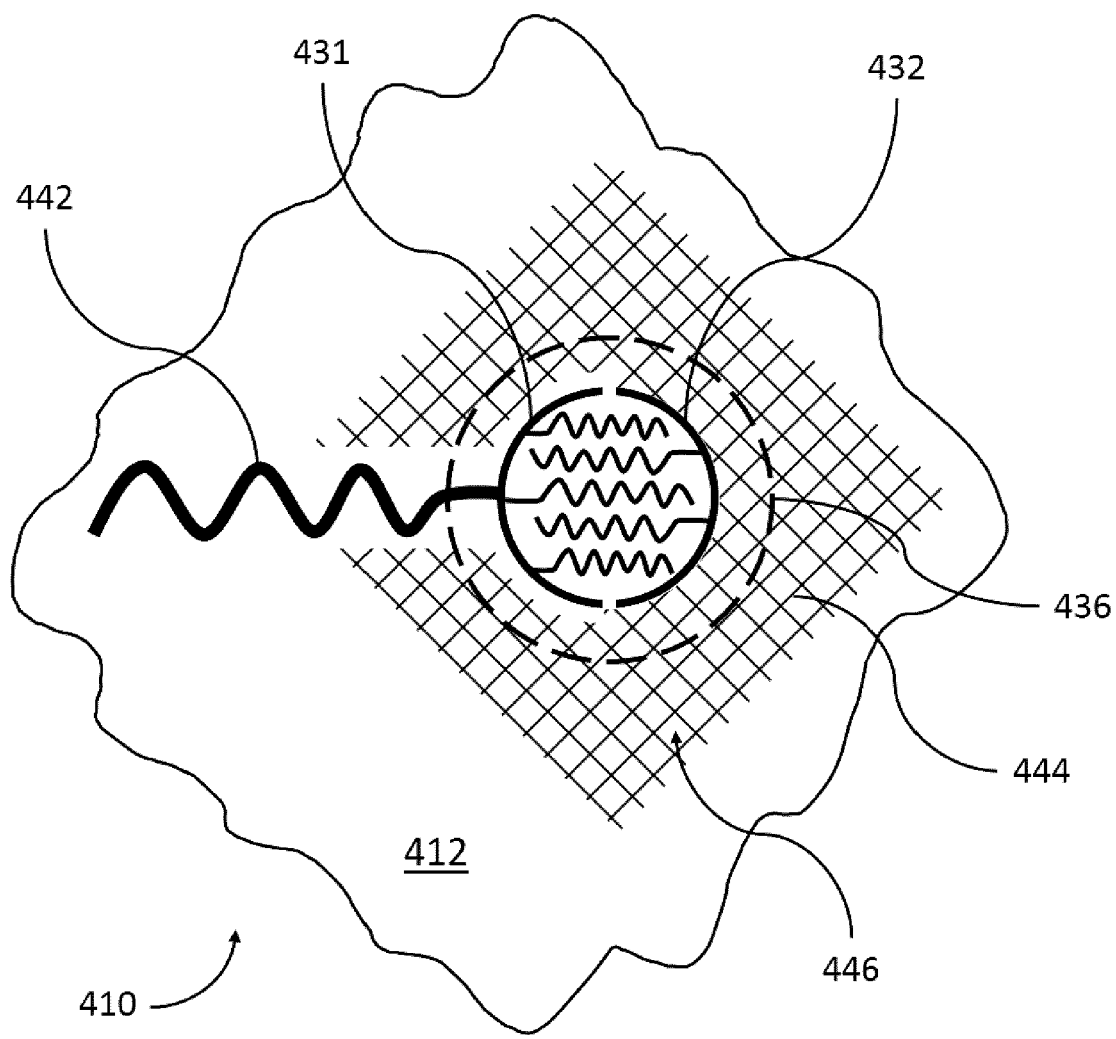
FIG. 9 is a plan view of a force-sensitive area in a flexible circuit package.

FIG. 9 shows a portion of a circuit package 410. The circuit package 410 would include the general features shown in the circuit packages 10, 110 of FIGS. 1 to 6. The connection trace 442, the first electrode 431, and the second electrode 432 are each connected with the substrate in a meandering pattern for mitigating breaks when the base substrate 412 is flexed or bent. Other shapes may also be applied to similarly spread out the effects of flex on the conductive material 440 (e.g. serpentine, maze-like, etc.).

Figure 10:
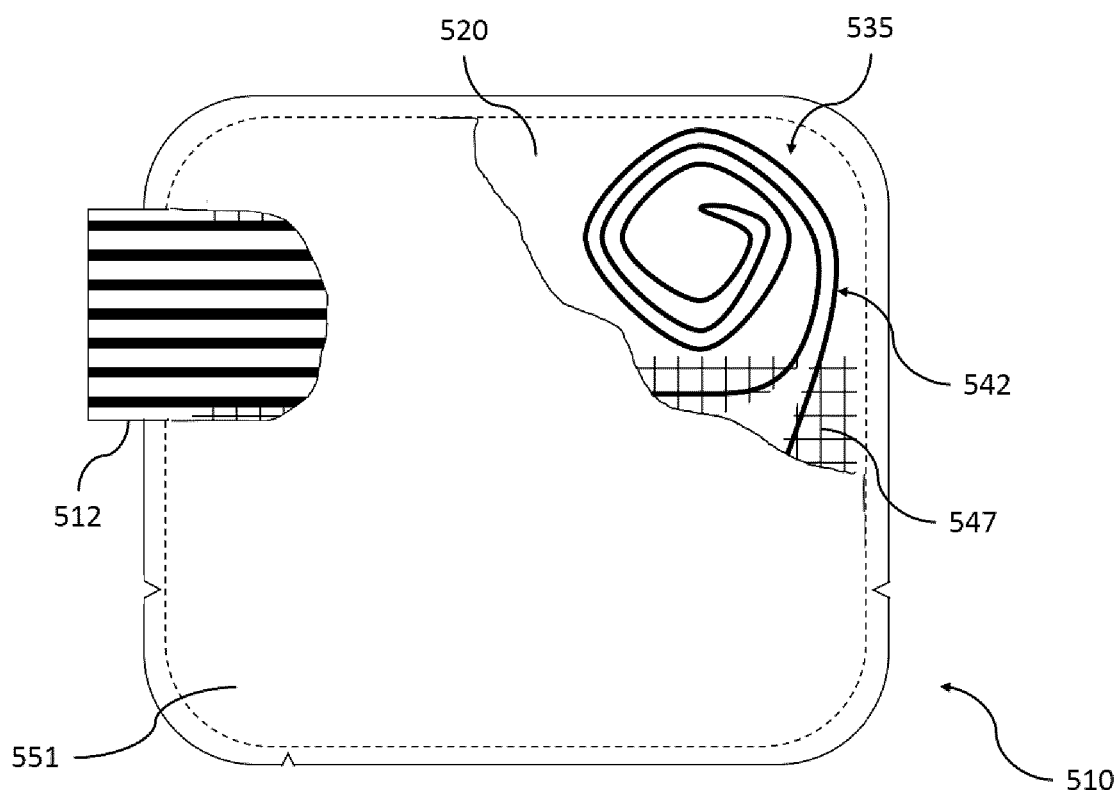
FIG. 10 is a plan view of a flexible circuit package.

FIG. 10 shows a circuit package 510. A deformation sensor 535 may be applied rather than the pressure sensor 30 of the circuit package 10. The deformation sensor 535 may be patterned onto the base substrate 520, which in the circuit package 510 includes only a single layer, to cover a large portion of the surface area of the circuit package 510. Changes in electrical characteristics of the deformation sensor 535, such as the resistance, capacitance, conductance, inductance, or a combination thereof, of the deformation sensor 535, are monitored following deformation of the circuit package 510. An interconnected reinforcement 547 may be included in the connection traces 542 between the deformation sensor 535 and an output interface 512.

Figure 11:
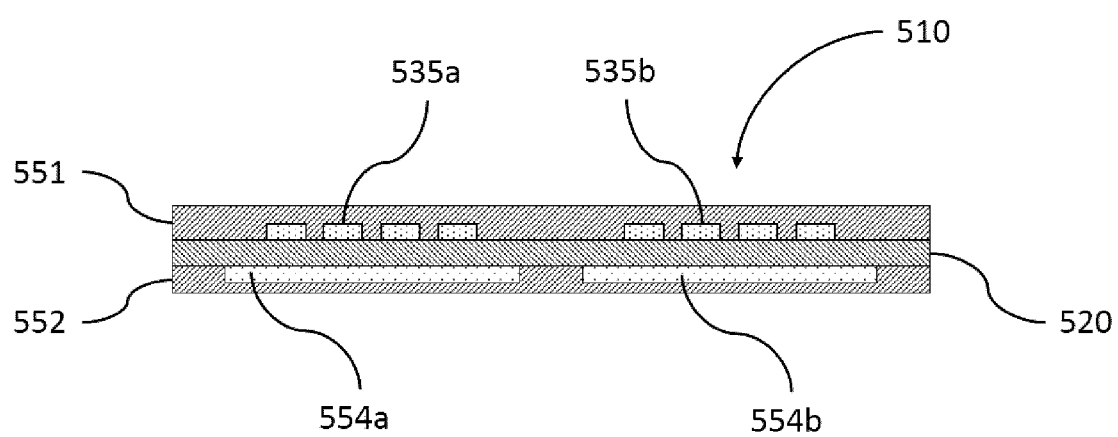
FIG. 11 is a cross-section elevation view of the package of FIG. 10.

FIG. 11 shows the circuit package 510 in cross section. The deformation sensor 535 is connected with the base substrate 520 and covered by the first protective layer 551. The reinforcement elements 554 are included below the deformation sensors 535 and covered by the second protective layer 552. The reinforcement elements 554 may reduce flexion of the package 510 at the deformation sensor 535, which in addition to mitigating damage to the deformation sensor 535 may also provide some control over the calibration range of the deformation sensor 535.

Figure 12:
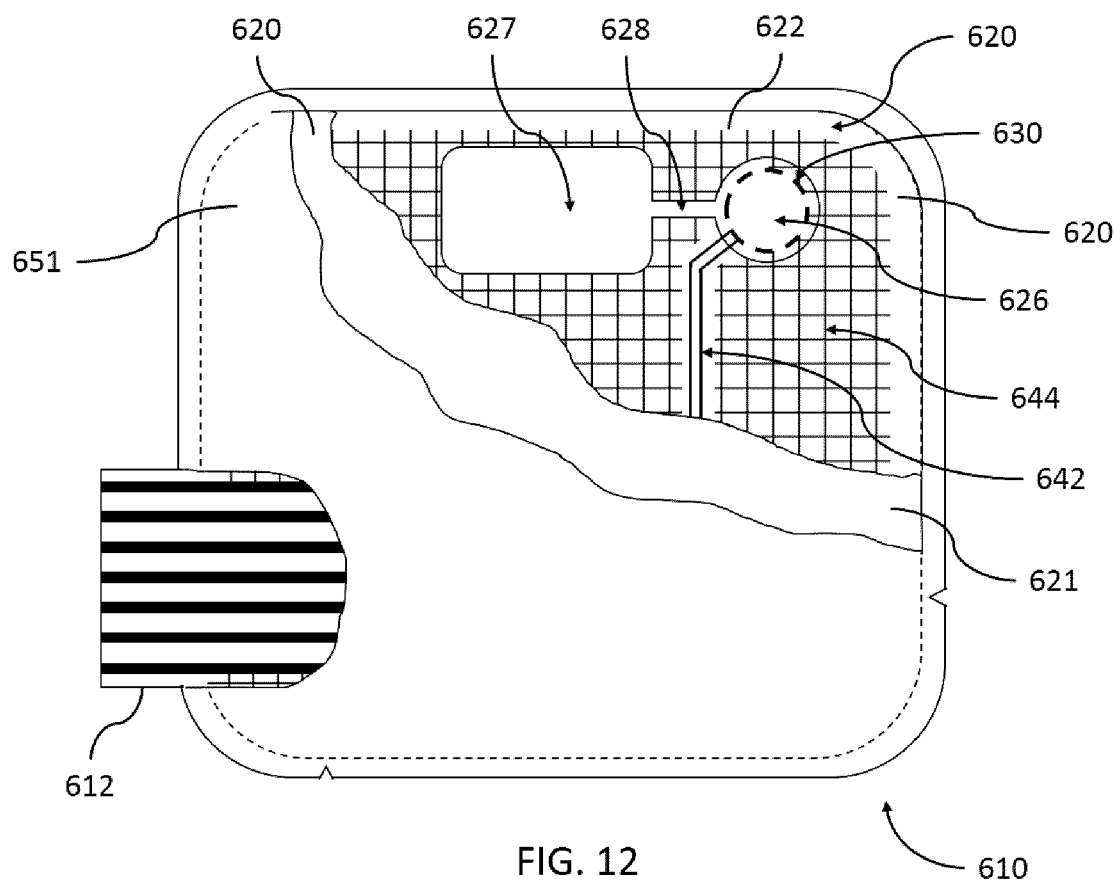
FIG. 12 is a plan view of a flexible circuit package.

FIG. 12 shows a circuit package 610. The sensor 630 is located on the base substrate 620, which includes the first base substrate layer 621 and the second base substrate layer 622. The conductive material 640 is connected with the first base substrate layer 621. The protective cover 650 is located externally to the base substrate 620 and the conductive material 640 for mitigating damage to the conductive material 640 or the base substrate 620. The protective cover 650 includes the first protective layer 651 and the second protective layer 652. The connection traces 642 connect the sensors 630 to the output interface 612 for connecting the circuit package 610 to measurement electronics. The sensors 630 may include pressure sensors but other suitable sensors may also be applied. The patterned interconnects 644 are defined with void spaces 646 in between leads of the conductive material 640 for mitigating propagation of cracks in the conductive material 640 during flexion of the circuit package 610. Acting as rip-stops, the void spaces 646 provide breakpoints across the surface of the conductive material 640, slowing crack propagation and facilitating maintaining the electrical integrity of any connection including the patterned interconnects 644 during and following flexion, stretching, compression or other deformation of the circuit package 610.

The fluid channels 628 do not extend to the external air, but rather to pre-formed fluid reservoirs 627 that include air, nitrogen, a liquid or any suitable fluid. The fluid reservoirs 627 are formed between the first base substrate layer 621 and the second base substrate layer 622, and within the spacer material (not shown; similar to the spacer material 56 of the circuit package 10). The fluid reservoirs 627 allow for the compression of fluid necessary for the sensors 630 to displace appropriately, without being open to external air, allowing control over humidity and resulting air pressure within fluid reservoirs 627 and the chamber 626.

FIG. 13 shows a circuit package 710. Sensors 730a, 730b and 730c are distributed across the base substrate 720, which includes the first base substrate layer 721 and the second base substrate layer 722. The conductive material 740 is connected with the first base substrate layer 721. The protective cover 750 is located externally to the base substrate 720 and the conductive material 740 for mitigating damage to the conductive material 740 or the base substrate 720. The protective cover 750 includes the first protective layer 751 and the second protective layer 752. Connection traces 742a, 742b and 742c respectively connect the sensors 730a, 730b and 730c to the output interface 712 for connecting the circuit package 710 to measurement electronics. The sensors 730a, 730b and 730c may include pressure sensors but other suitable sensors may also be applied. The patterned interconnects 744a, 744b and 744c are defined with void spaces 746 in between leads of the conductive material 740 for mitigating propagation of cracks in the conductive material 740 during flexion of the circuit package 710. Acting as rip-stops, the void spaces 746 provide breakpoints across the surface of the conductive material 740, slowing crack propagation and facilitating maintaining the electrical integrity of any connection including the patterned interconnects 744 during and following flexion, stretching, compression or other deformation of the circuit package 710.

The circuit package 710 includes an interconnected reinforcement 749 in the connection traces 742. The interconnected reinforcement 749 may provide additional connections and voids at areas of greater expected flexion 724, such as the expected axis of flexion 724 introduced in the package 710 by the relief cuts 725. Reinforcement elements (not shown; analogous to the reinforcement elements 54 of the circuit package 10 and the reinforcement elements 554 of the package 510) could be included on the interconnected reinforcement 749.

Figure 14:
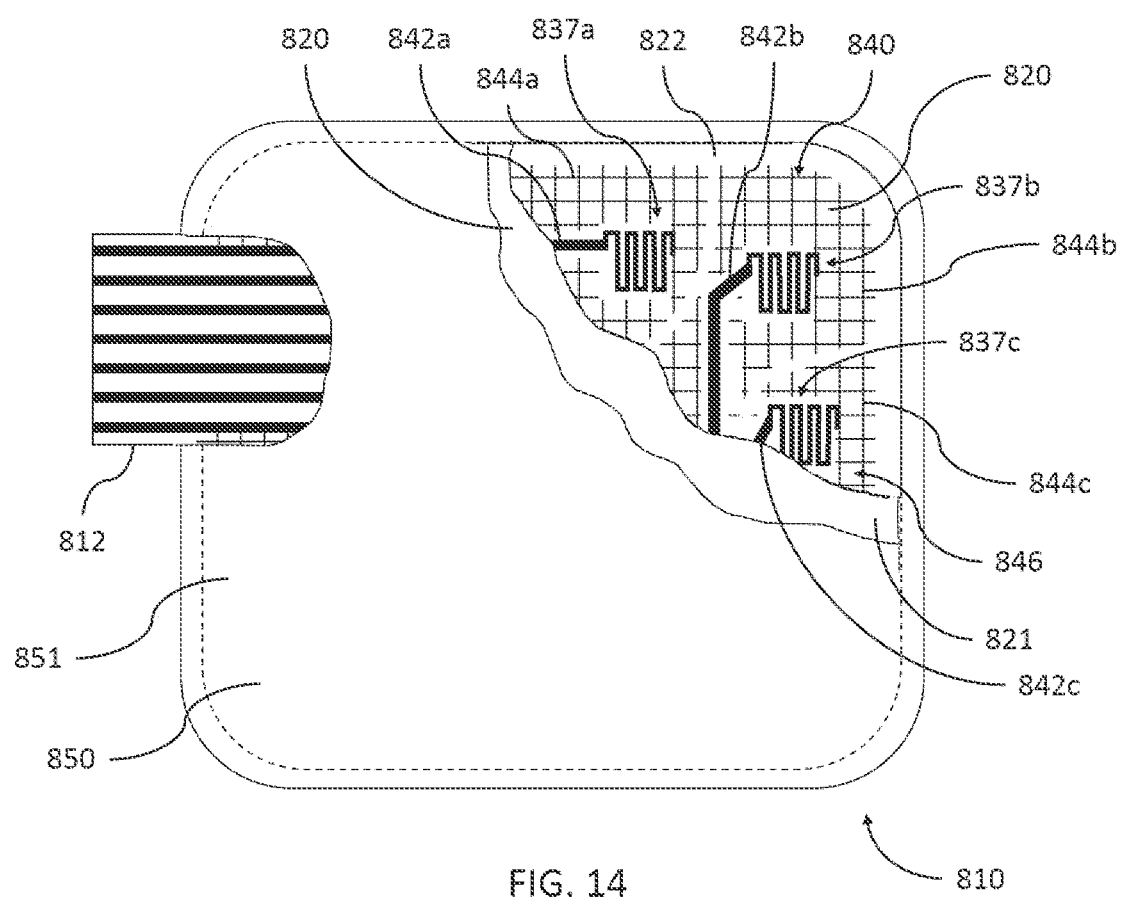
FIG. 14 is a plan view of a flexible circuit package.

FIG. 14 shows a circuit package 810 including temperature sensors 837. Temperature sensors 837a, 837b and 837c are distributed across the base substrate 820, which includes the first base substrate layer 821 and the second base substrate layer 822. The conductive material 840 is connected with the first base substrate layer 821. The protective cover 850 is located externally to the base substrate 820 and the conductive material 840 for mitigating damage to the conductive material 840 or the base substrate 820. The protective cover 850 includes the first protective layer 851 and the second protective layer 852. Connection traces 842a, 842b and 842c respectively connect the temperature sensors 837a, 837b and 837c to an output interface 812 for connecting the circuit package 810 to measurement electronics. The temperature sensors 837a, 837b and 837c may include pressure sensors but other suitable sensors may also be applied. The patterned interconnects 844a, 844b and 844c are defined with void spaces 846 in between leads of the conductive material 840 for mitigating propagation of cracks in the conductive material 840 during flexion of the circuit package 810. Acting as rip-stops, the void spaces 846 provide breakpoints across the surface of the conductive material 840, slowing crack propagation and facilitating maintaining the electrical integrity of any connection including the patterned interconnects 844 during and following flexion, stretching, compression or other deformation of the circuit package 810. The temperature sensors 837 may be included in a circuit package that also includes the pressure sensors, deformation sensors or other sensors.

Figure 15:
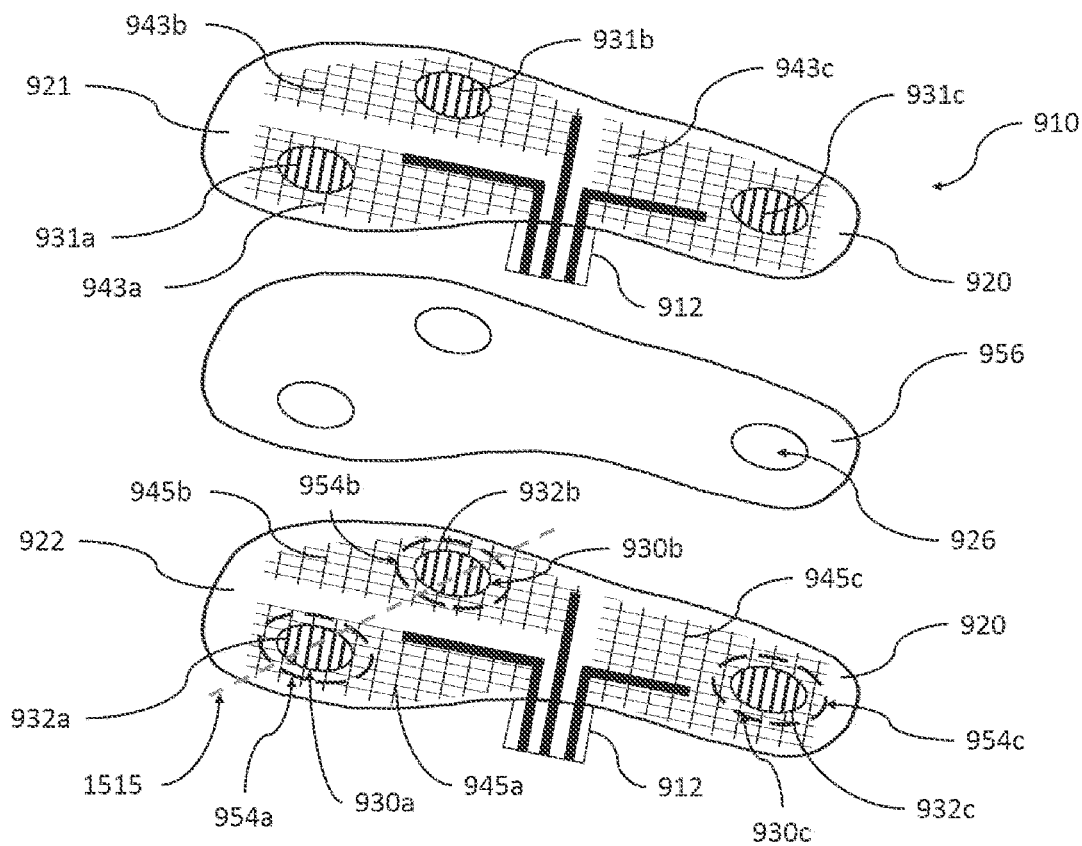
FIG. 15 an exploded view of a flexible circuit package for use as an insole.
Figure 16:
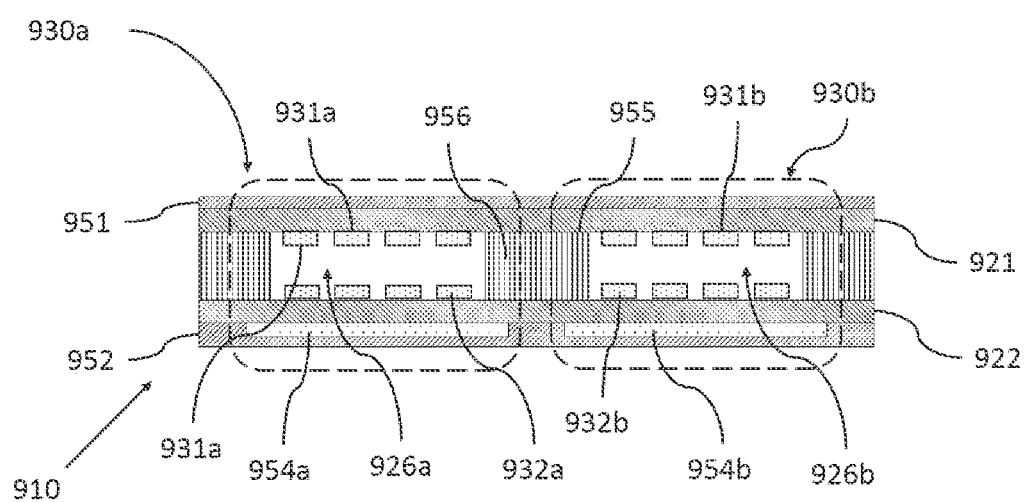
FIG. 16 is a cross-section elevation view of the flexible circuit package of FIG. 15.

FIGS. 15 and 16 show a circuit package 910 with a through-mode sensor 930. Sensors 930a, 930b and 930c are distributed across the base substrate 920, which includes the first base substrate layer 921 and the second base substrate layer 922. The circuit package 910 is shaped for use as an insole. The protective cover 950 is located externally to the base substrate 920 and the conductive material 940 for mitigating damage to the conductive material 940 or the base substrate 920. The protective cover 950 includes the first protective layer 951 and the second protective layer 952.

The first patterned interconnects 943a, 943b and 943c respectively connect the first electrodes 931a, 931b and 931c to the output interface 912 for connecting the circuit package 910 to measurement electronics. The second patterned interconnects 945a, 945b and 945c respectively connect the second electrodes 932a, 932b and 932c to the output interface 912 for connecting the circuit package 910 to measurement electronics. The sensors 930a, 930b and 930c may include pressure sensors but other suitable sensors may also be applied. The first patterned interconnects 943a, 943b and 943c and the second patterned interconnects 945a, 945b and 945c are defined with the void spaces 946 in between leads of the conductive material 940 for mitigating propagation of cracks in the conductive material 940 during flexion of the circuit package 910. Acting as rip-stops, the void spaces 946 provide breakpoints across the surface of the conductive material 940, slowing crack propagation and facilitating maintaining the electrical integrity of any connection including the patterned interconnects 944 during and following flexion, stretching, compression or other deformation of the circuit package 910.

The first electrodes 931a, 931b and 931c and the patterned interconnects 943a, 943b and 943c forming the first circuit are connected with the first base substrate layer 921. The second electrode 932a, 932b and 932c and the second patterned interconnects 945a, 945b and 945c forming the second circuit are connected with the second base substrate layer 922. The spacer 956 is located between the first base substrate layer 921 and the second base substrate layer 922 around the footprint of the pressure sensor 930. The spacer 956 is bonded to the first layer and the second layer by adhesive 955. The spacer 956 introduces a gap between the first base substrate layer 921 and the second base substrate layer 922, defining the chambers 926a, 926b and 926c between the first electrode 931 connected with the first base substrate layer 921 and the second electrode 932 connected with the second base substrate layer 922.

The conductive material 940 is connected with the first base substrate layer 921 and with the second base substrate layer 922. The first electrode 931 is connected with the first substrate layer 921 and the second electrode 932 is connected with the second substrate layer 922. Under pressure, the first electrode 931 is urged into contact with the second electrode 932 across the chamber 926.

Figure 17:
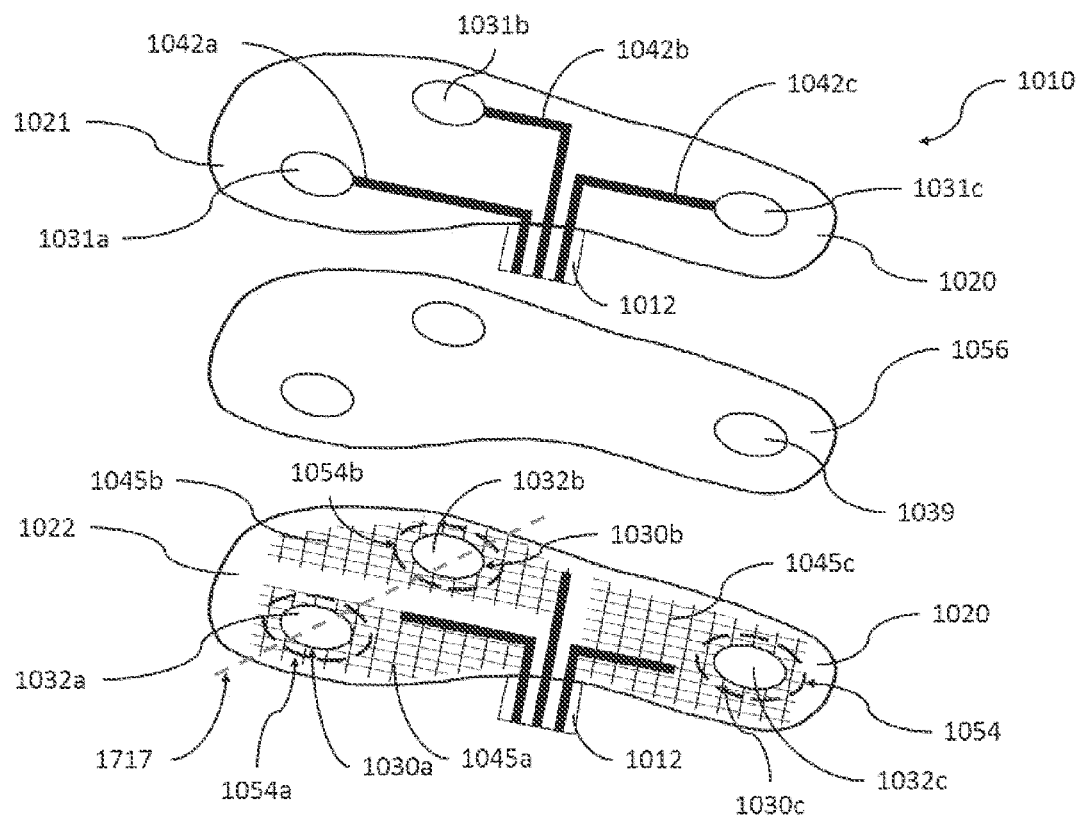
FIG. 17 is an exploded view of a flexible circuit package for use as an insole.
Figure 18:
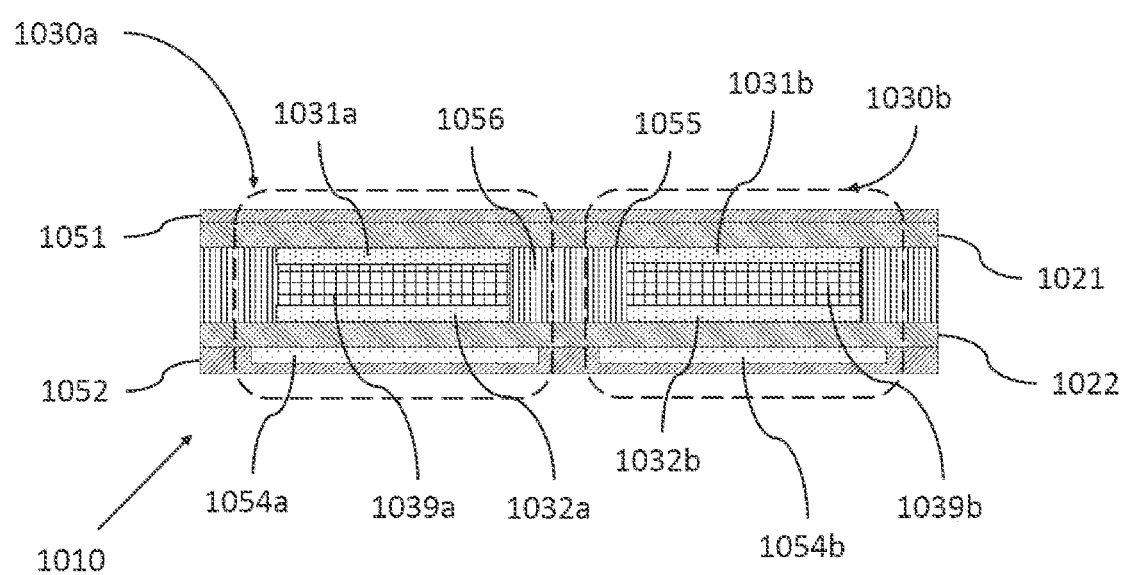
FIG. 18 is a cross-section elevation view of the flexible circuit package of FIG. 17.

FIGS. 17 and 18 show a circuit package 1010 with a capacitive sensor 1030. Sensors 1030a, 1030b and 1030c are distributed across the base substrate 1020, which includes the first base substrate layer 1021 and the second base substrate layer 1022. The circuit package 1010 is shaped for use as an insole. The conductive material 1040 is connected with the first base substrate layer 1021. The protective cover 1050 is located externally to the base substrate 1020 and the conductive material 1040 for mitigating damage to the conductive material 1040 or the base substrate 1020. The protective cover 1050 includes the first protective layer 1051 and the second protective layer 1052. The connection traces 1042a, 1042b and 1042c respectively connect the sensors 1030a, 1030b and 1030c to the output interface 1012 for connecting the circuit package 1010 to measurement electronics. The patterned interconnects 1045a, 1045b and 1045c respectively connect the sensors 1030a, 1030b and 1030c to the output interface 1012. The sensors 1030a, 1030b and 1030c may include pressure sensors but other suitable sensors may also be applied. The patterned interconnects 1045a, 1045b and 1045c are defined with void spaces 1046 in between leads of the conductive material 1040 for mitigating propagation of cracks in the conductive material 1040 during flexion of the circuit package 1010. Acting as rip-stops, the void spaces 1046 provide breakpoints across the surface of the conductive material 1040, slowing crack propagation and facilitating maintaining the electrical integrity of any connection including the patterned interconnects 1045a, 1045b and 1045c during and following flexion, stretching, compression or other deformation of the circuit package 1010. Reinforcement elements 1054a and 1054b are included between the second base substrate layer 1022 and the second protective layer 1052 under each sensor 1030a and 1030b.

The first electrodes 1031a, 1031b and 1031c, and the connection traces 1042 forming the first circuit are connected with the first base substrate layer 1021. The second electrodes 1032a, 1032b and 1032c, and the patterned interconnects 1045a, 1045b and 1045c forming the second circuit are connected with the second base substrate layer 1022. The spacer 1056 is located between the first base substrate layer 1021 and the second base substrate layer 1022 around the footprint of the pressure sensor 1030. The spacer 1056 is bonded to the first layer and the second layer by adhesive 1055. The spacer 1056 introduces a gap between the first base substrate layer 1021 and the second base substrate layer 1022, and defining the chambers 1026a, 1026b and 1026c between the first electrode 1031 and the second electrode 1032 connected with the first base substrate layer 1021.

A dielectric spacer 1039 is located between the first electrode 1031 and the second electrode 1032, which do not fully contact each other either directly or through a conductor bridge. Rather, when the sensor 1030 is compressed, the first electrode 1031 and the second electrode 1032 are urged close to one another, compressing the dielectric spacer 1039, resulting in a measurable change in capacitance.

Figure 19:
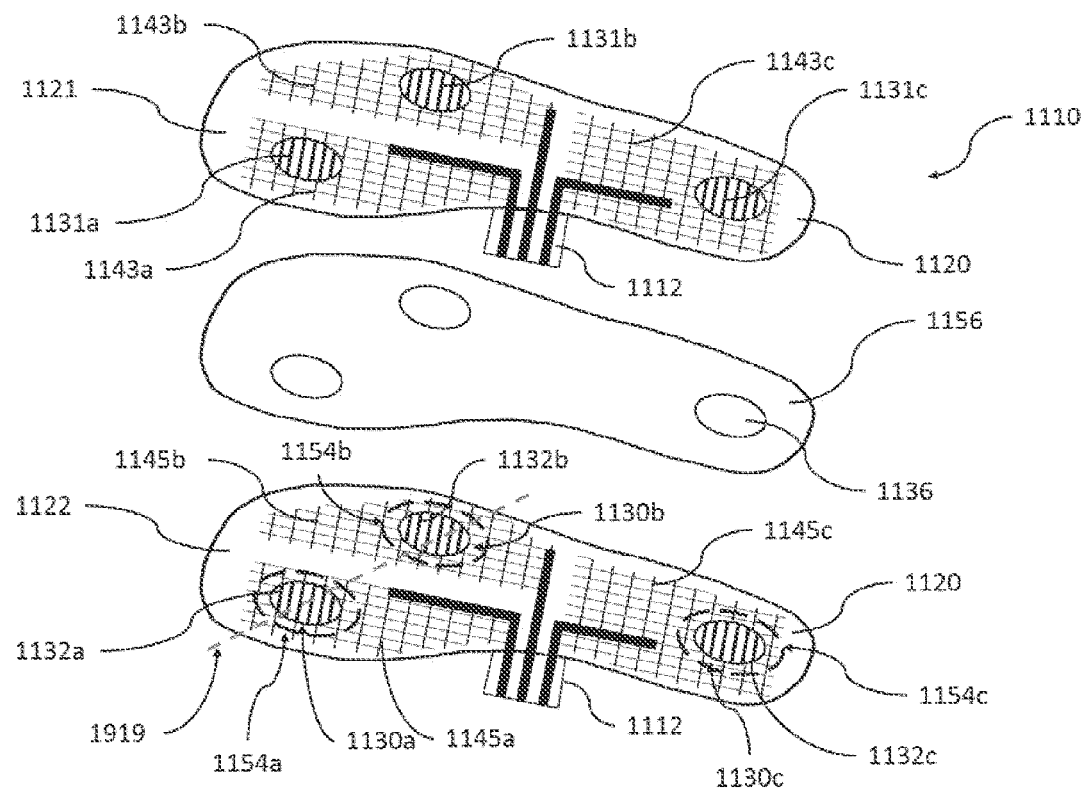
FIG. 19 is an exploded view of a flexible circuit package for use as an insole.
Figure 20:
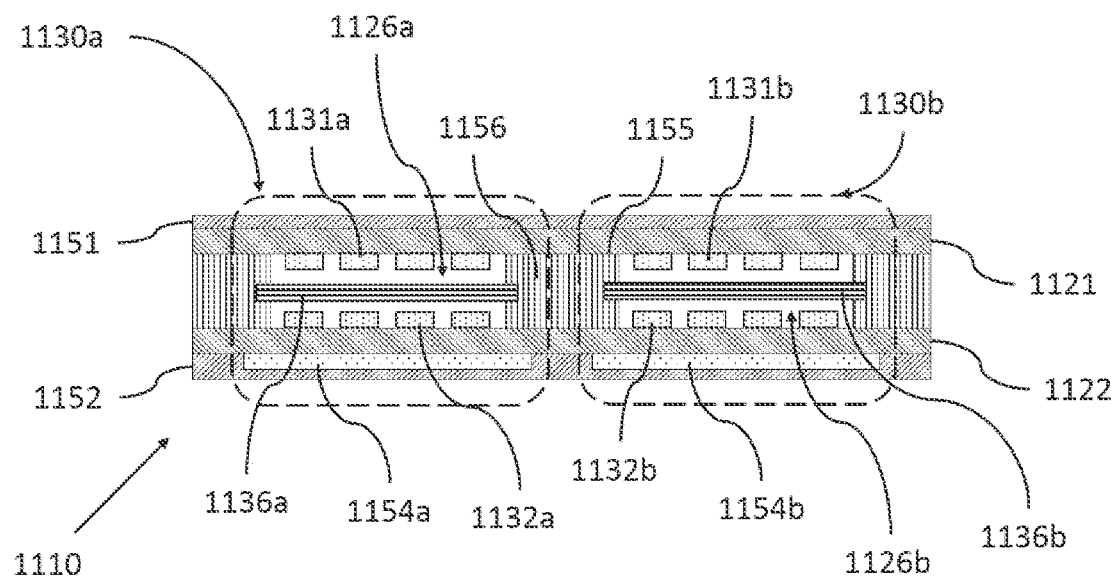
FIG. 20 is a cross-section elevation view of the flexible circuit package of FIG. 19.

FIGS. 19 and 20 show a circuit package 1110. Sensors 1130a, 1130b and 1130c are distributed across the base substrate 1120, which includes the first base substrate layer 1121 and the second base substrate layer 1122. The circuit package 1110 is shaped for use as an insole. The protective cover 1150 is located externally to the base substrate 1120 and the conductive material 1140 for mitigating damage to the conductive material 1140 or the base substrate 1120. The protective cover 1150 includes the first protective layer 1151 and the second protective layer 1152. Connection traces 1142a, 1142b and 1142c respectively connect the sensors 1130a, 1130b and 1130c to the output interface 1112 for connecting the circuit package 1110 to measurement electronics. The sensors 1130a, 1130b and 1130c may include pressure sensors but other suitable sensors may also be applied. The patterned interconnects 1144a, 1144b and 1144c are defined with void spaces 1146 in between leads of the conductive material 1140 for mitigating propagation of cracks in the conductive material 1140 during flexion of the circuit package 1110. Acting as rip-stops, the void spaces 1146 provide breakpoints across the surface of the conductive material 1140, slowing crack propagation and facilitating maintaining the electrical integrity of any connection including the patterned interconnects 1144 during and following flexion, stretching, compression or other deformation of the circuit package 1110.

The first patterned interconnects 1143a, 1143b and 1143c respectively connect the first electrodes 1131a, 1131b and 1131c to the output interface 1112 for connecting the circuit package 1110 to measurement electronics. The second patterned interconnects 1145a, 1145b and 1145c respectively connect the second electrodes 1132a, 1132b and 1132c to the output interface 1112 for connecting the circuit package 1110 to measurement electronics. The sensors 1130a, 1130b and 1130c may include pressure sensors but other suitable sensors may also be applied. The first patterned interconnects 1143a, 1143b and 1143c and the second patterned interconnects 1145a, 1145b and 1145c are defined with the void spaces 1146 in between leads of the conductive material 1140 for mitigating propagation of cracks in the conductive material 1140 during flexion of the circuit package 1110. Acting as rip-stops, the void spaces 1146 provide breakpoints across the surface of the conductive material 1140, slowing crack propagation and facilitating maintaining the electrical integrity of any connection including the patterned interconnects 1144 during and following flexion, stretching, compression or other deformation of the circuit package 1110.

The first electrodes 1131a, 1131b and 1131c, and the patterned interconnects 1143a, 1143b and 1143c forming the first circuit are connected with the first base substrate layer 1122. The second electrodes 1132a, 1132b and 1132c, and the second patterned interconnects 1145a, 1145b and 1145c forming the second circuit are connected with the second base substrate layer 1121. The spacer 1156 is located between the first base substrate layer 1121 and the second base substrate layer 1122 around the footprint of the pressure sensor 1130. The spacer 1156 is bonded to the first layer and the second layer by adhesive 1155. The spacer 1156 introduces a gap between the first base substrate layer 1121 and the second base substrate layer 1122, defining the chambers 1126a, 1126b and 1126c between the first electrode 1131 connected with the first base substrate layer 1121 and the second electrode 1132 connected with the second base substrate layer 1122.

The conductor bridge 1136a is positioned in the chamber 1126a between the first electrode 1131a and the second electrode 1132a. The conductor bridge 1136b is positioned in the chamber 1126b between the first electrode 1131b and the second electrode 1132b. Under pressure, the first electrodes 1131a and 1131b, and the second electrodes 1132a and 1132b, are each urged into contact with the conductor bridges 1136a and 1136b, across the chambers 1126a and 1126b.

Figure 21:
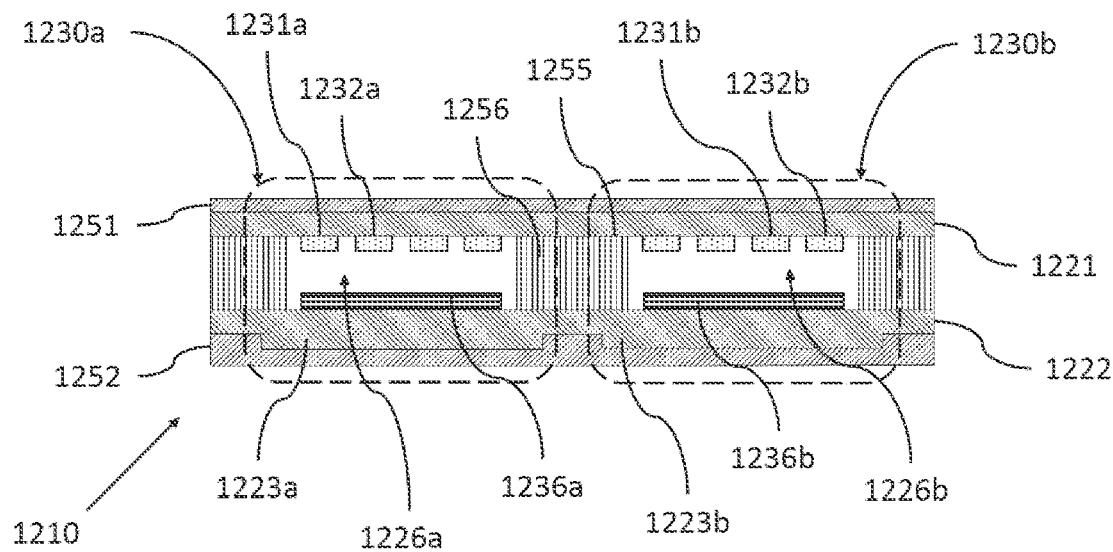
FIG. 21 is a cross-section elevation view of a flexible circuit package.

FIG. 21 shows a cross section of the circuit package 1210 showing the sensors 1230a and 1230b, illustrating the first base substrate layer 1221 and the second base substrate layer 1222. The first electrodes 1231a and 1231b are connected with the first base substrate layer 1221. The second electrodes 1232a and 1232b, are also connected with the first base substrate layer 1221. Further conductive material 1240 is added as conductor bridges 1236a and 1236b to the second base substrate layer 1222. A spacer 1256 is located between the first base substrate layer 1221 and the second base substrate layer 1222 around the footprints of the pressure sensors 1230a and 1230b, introducing a gap between the first base substrate layer 1221 and the second base substrate layer 1222, and defining a chamber 1226a between the first electrode 1231a and the second electrode 1232a connected with the first base substrate layer 1221, and the conductor bridge 1236a connected with the second base substrate layer 1222. Similarly, the chamber 1226b is formed between the first electrode 1231b and the second electrode 1232b connected with the first base substrate layer 1221, and the conductor bridge 1236b connected with the second base substrate layer 1222.

When pressure is applied to the circuit package 1210 at the sensor 1230a, the first electrode 1231a and the second electrode 1232a are pushed through the chamber 1226a and contact the opposing conductor bridge 1236a. Thus, the first electrode 1231a and the second electrode 1232a are brought into electrical contact with one another through the conductor bridge 1236a. The greater the applied pressure, the smaller the electrical resistance between the first electrode 1231a and the second electrode 1232a, as larger portions of each of their respective surface areas contact the opposing conductor bridge 1236a. The first electrode 1231b and the second electrode 1232b are similarly brought into contact with the opposing conductor bridge 1236b when the sensor 1230b is under pressure.

The second substrate layer 1222 is a continuous layer of base substrate with various thicknesses that are used to reinforce portions of the base circuit package 1210 with additional rigidity at reinforced portions 1223a and 1223b. The reinforced portions 1223a and 1223b are prepared from the same material as the rest of the second substrate layer 1222 but have greater thickness for increased rigidity and reinforcement.

Figure 22:
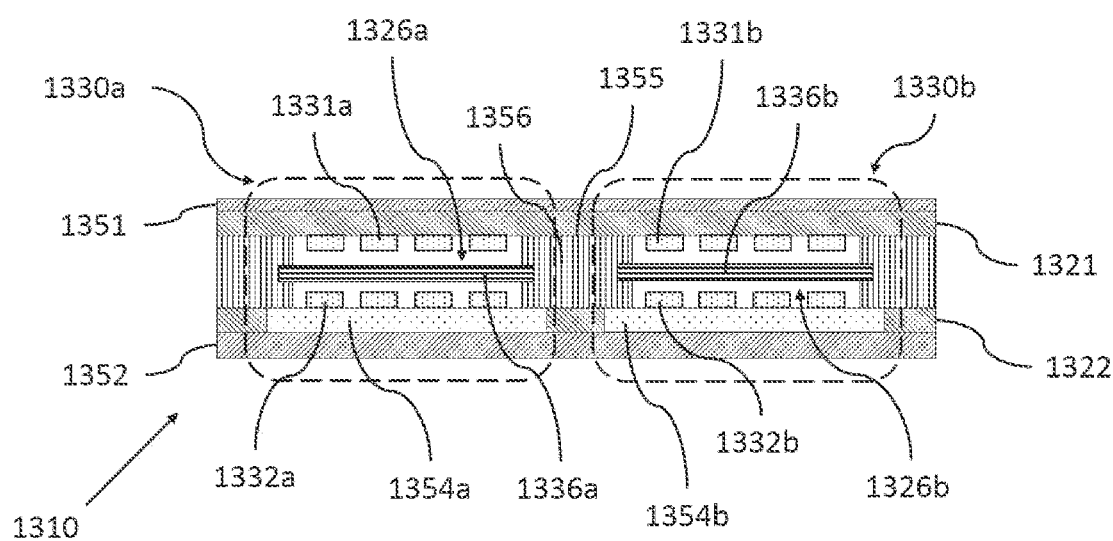
FIG. 22 is a cross-section elevation view of a flexible circuit package.

FIG. 22 is shows a cross section of the circuit package 1310 showing the sensors 1330a and 1330b, illustrating the first base substrate layer 1321 and the second base substrate layer 1322. The first electrodes 1331a and 1331b are connected with the first base substrate layer 1321. The second electrodes 1332a and 1332b, are connected directly with the reinforcement elements 1354a and 1354b, rather than to the second base substrate layer 1322. The spacer 1356 is located between the first base substrate layer 1321 and the second base substrate layer 1322 around the footprints of the pressure sensors 1330a and 1330b, introducing a gap between the first base substrate layer 1321 and the second base substrate layer 1322, and defining the chamber 1326a between the first electrode 1331a and the second electrode 1332a connected with the first base substrate layer 1321, and the conductor bridge 1336a connected with the second base substrate layer 1322. Similarly, the chamber 1326b is formed between the first electrode 1331b and the second electrode 1332b connected with the first base substrate layer 1321, and the conductor bridge 1336b connected with the second base substrate layer 1322. Further conductive material 1340 is added as conductor bridges 1336a and 1336b. The conductor bridges 1336a and 1336b are anchored within the spacer 1356 and respectively extend through the chambers 1326a and 1326b.

The conductor bridge 1336a is positioned in the chamber 1326a between the first electrode 1331a and the second electrode 1332a. The conductor bridge 1336b is positioned in the chamber 1326b between the first electrode 1331b and the second electrode 1232b. Under pressure, the first electrodes 1331a and 1331b, and the second electrodes 1332a and 1332b, are each urged into contact with the conductor bridges 1336a and 1336b, across the chambers 1326a and 1326b.

The reinforcement elements 1354a and 1354b are included as part of the second substrate layer 1322 rather than below the second substrate layer 1322. This may facilitate a lower-profile circuit package 1310 than in a circuit package with the reinforcement elements below the second substrate layer.

Figure 23:
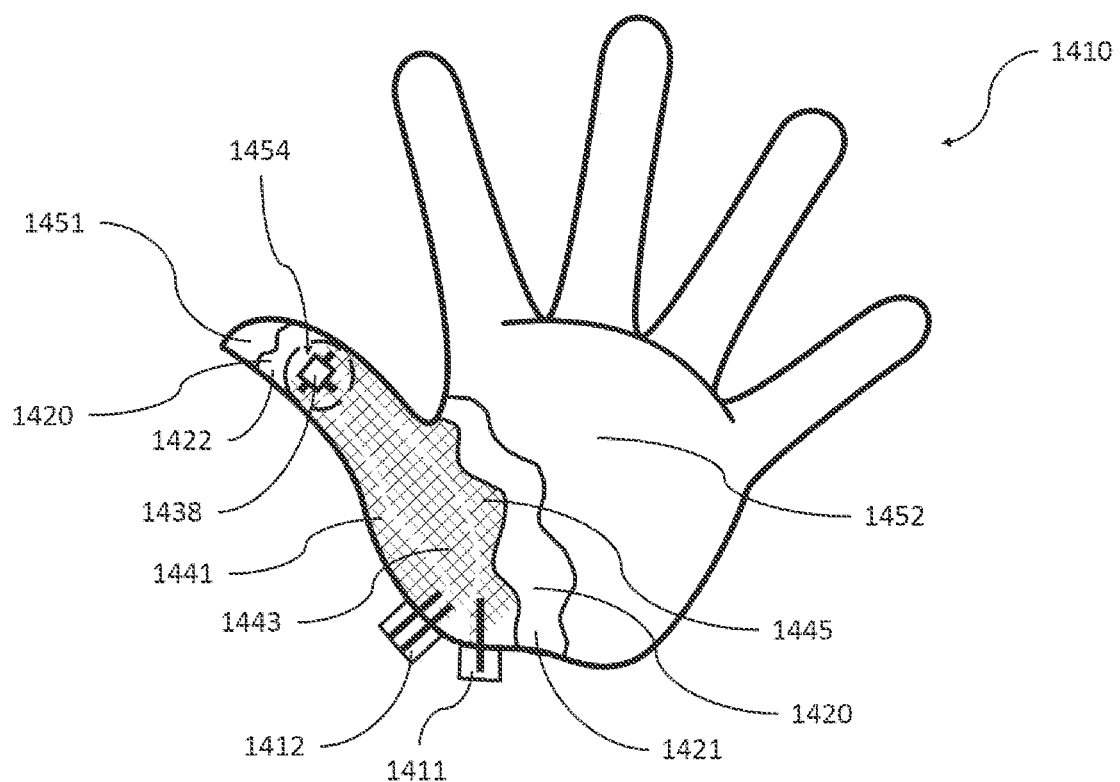
FIG. 23 is a partial cutaway view of a flexible circuit package for use as a glove.

FIG. 23 is a circuit package 1410 shaped for use as a glove. A switch 1438 is connected with the base substrate 1420, which includes the first base substrate layer 1421 and the second base substrate layer 1422. The conductive material 1440 is connected with the first base substrate layer 1421. The protective cover 1450 is located externally to the base substrate 1420 and the conductive material 1440 for mitigating damage to the conductive material 1440 or the base substrate 1420. The protective cover 1450 includes the first protective layer 1451 and the second protective layer 1452.

The first patterned interconnect 1441, the second patterned interconnect 1443 and a third patterned interconnect 1445 each connect to the switch 1438. The first patterned interconnect 1441 and the second patterned interconnect 1443 each connect with the output interface 1412 for connecting the circuit package 1410 to measurement electronics. The third patterned interconnect 1445 connects with a power module 1411 for powering the switch 1438.

The first patterned interconnect 1441, the second patterned interconnect 1443 and the third patterned interconnect 1445 are each defined with void spaces 1446 in between leads of the conductive material 1440 for mitigating propagation of cracks in the conductive material 1440 during flexion of the circuit package 1410. Acting as rip-stops, the void spaces 1446 provide breakpoints across the surface of the conductive material 1440, slowing crack propagation and facilitating maintaining the electrical integrity of any connection including the first patterned interconnect 1441, the second patterned interconnect 1443 and the third patterned interconnect 1445 during and following flexion, stretching, compression or other deformation of the circuit package 1410. Maintaining electrical communication between the output interface 1412 and the switch 1438 during and following flexion, stretching, compression or other deformation of the circuit package 1410 may be facilitated by the first patterned interconnect 1441, the second patterned interconnect 1443 and the third patterned interconnect 1445.

Figure 24:
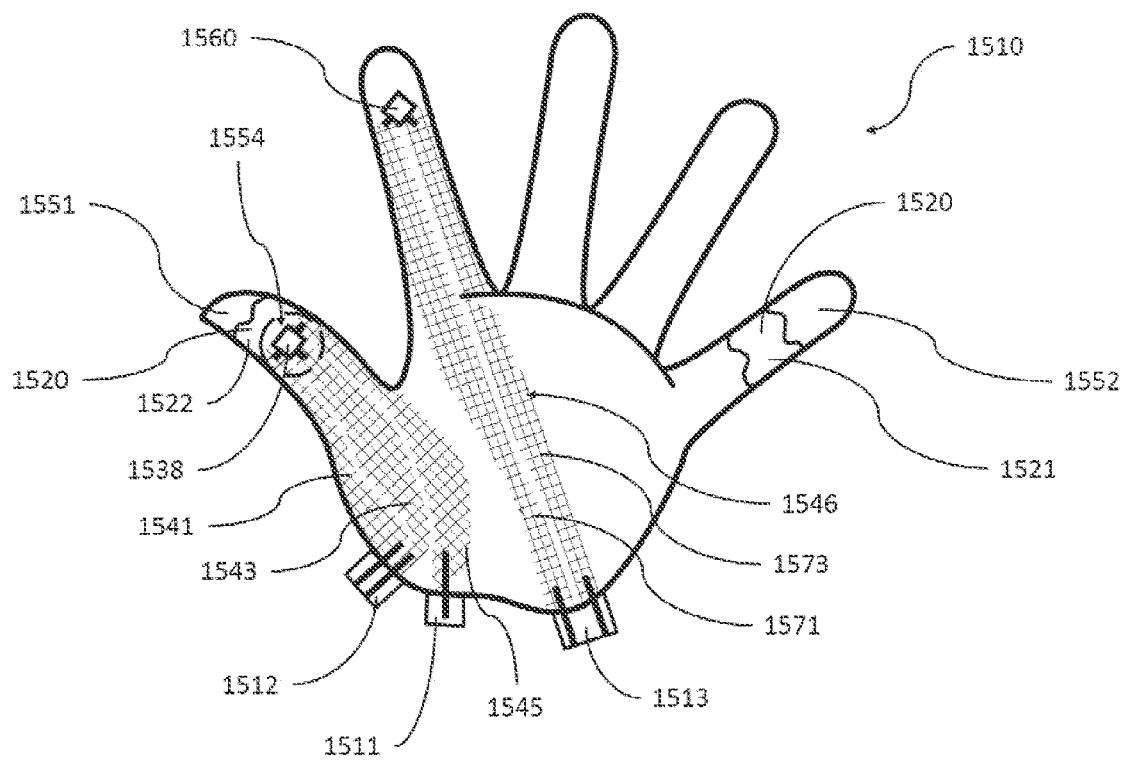
FIG. 24 is a partial cutaway view of a flexible circuit package for use as a glove.

FIG. 24 is a circuit package 1510 shaped for use as a glove. The switch 1538 is connected with the base substrate 1520, which includes the first base substrate layer 1521 and the second base substrate layer 1522. The conductive material 1540 is connected with the first base substrate layer 1521. The protective cover 1550 is located externally to the base substrate 1520 and the conductive material 1540 for mitigating damage to the conductive material 1540 or the base substrate 1520. The protective cover 1550 includes the first protective layer 1551 and the second protective layer 1552.

The first patterned interconnect 1541, the second patterned interconnect 1543 and the third patterned interconnect 1545 each connect to the switch 1538. The first patterned interconnect 1541 and the second patterned interconnect 1543 each connect with the output interface 1512 for connecting the circuit package 1510 to measurement electronics. The third patterned interconnect 1545 connects with a power module 1511 for powering the switch 1538.

A light 1560 is located at the tip of an index finger portion of the circuit package 1510. A fourth patterned interconnect 1571 and a fifth patterned interconnect 1573 provide electrical communication between an input interface 1513 and the light 1560. Commands from the input interface 1513 may activate, deactivate, change brightness, colour, flashing pattern or other properties of the light 1560, or may otherwise send signals to the light 1560. A transmission device, a speaker, a vibrator or other output module that changes state in response to a signal from the input interface 1513 may also be included as a termination point for the fourth patterned interconnect 1571 and the fifth patterned interconnect 1573.

The first patterned interconnect 1541, the second patterned interconnect 1543, the third patterned interconnect 1545, the fourth patterned interconnect 1571 and the fifth patterned interconnect 1573 are each defined with void spaces 1546 in between leads of the conductive material 1540 for mitigating propagation of cracks in the conductive material 1540 during flexion of the circuit package 1510. Acting as rip-stops, the void spaces 1546 provide breakpoints across the surface of the conductive material 1540, slowing crack propagation and facilitating maintaining the electrical integrity of any connection including the first patterned interconnect 1541, the second patterned interconnect 1543, the third patterned interconnect 1545, the fourth patterned interconnect 1571 and the fifth patterned interconnect 1573 during and following flexion, stretching, compression or other deformation of the circuit package 1510. Maintaining electrical communication between the output interface 1512 and the switch 1538 during and following flexion, stretching, compression or other deformation of the circuit package 1510 may be facilitated by first patterned interconnect 1541, the second patterned interconnect 1543, the third patterned interconnect 1545, the fourth patterned interconnect 1571 and the fifth patterned interconnect 1573.

Figure 25:
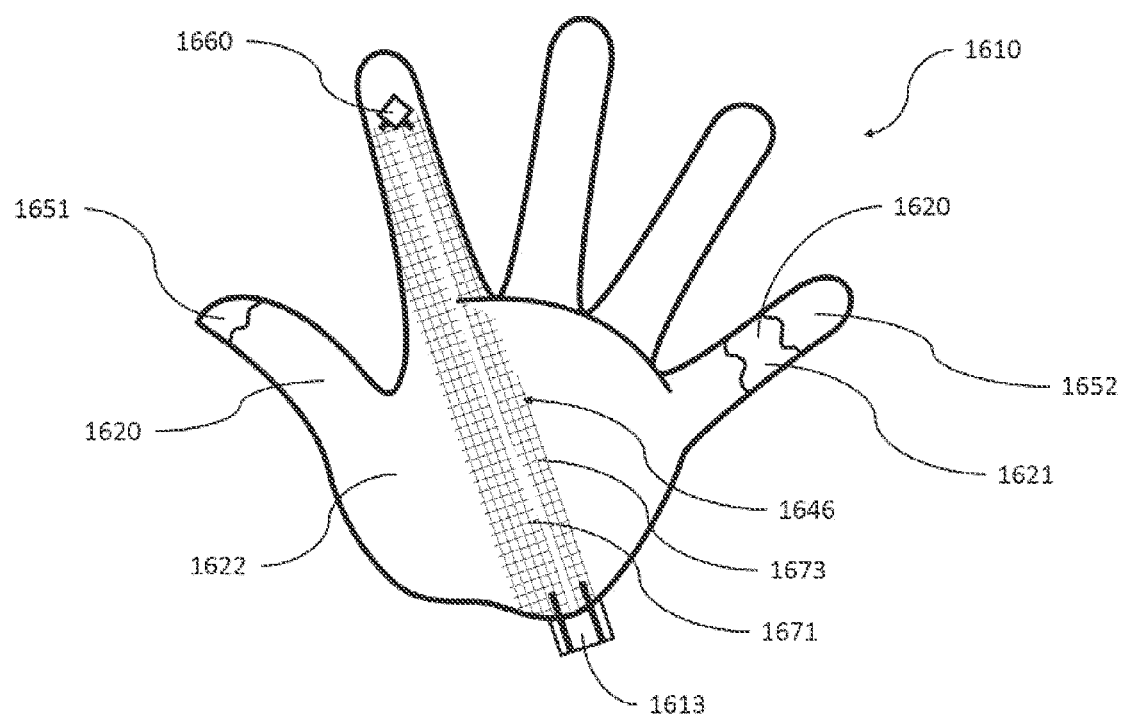
FIG. 25 is a partial cutaway view of a flexible circuit package for use as a glove.

FIG. 25 is a circuit package 1610 shaped for use as a glove. The light 1660 is located at the tip of an index finger portion of the circuit package 1610. A first patterned interconnect 1671 and a second patterned interconnect 1673 provide electrical communication between an input interface 1613 and the light 1660. The first patterned interconnect 1671 provides functionality similar to the fourth patterned interconnect 1671 in the flexible circuit package 1610. The second patterned interconnect 1673 provides functionality similar to the fifth patterned interconnect 1673 in the flexible circuit package 1610. Commands from the input interface 1613 may activate, deactivate, change brightness, colour, flashing pattern or other properties of the light 1660, or may otherwise send signals to the light 1660. A transmission device, a speaker, a vibrator or other output module that changes state in response to a signal from the input interface 1613 may also be included as a termination point for the fourth patterned interconnect 1671 and the fifth patterned interconnect 1673.

The first patterned interconnect 1671 and the second patterned interconnect 1673 are each defined with void spaces 1646 in between leads of the conductive material 1640 for mitigating propagation of cracks in the conductive material 1640 during flexion of the circuit package 1610. Acting as rip-stops, the void spaces 1646 provide breakpoints across the surface of the conductive material 1640, slowing crack propagation and facilitating maintaining the electrical integrity of any connection including the patterned interconnects 1644 during and following flexion, stretching, compression or other deformation of the circuit package 1610. Maintaining electrical communication between the output interface 1612 and the switch 1638 during and following flexion, stretching, compression or other deformation of the circuit package 1610 may be facilitated by the first patterned interconnect 1641, the second patterned interconnect 1643 and the third patterned interconnect 1645.

Figure 26:
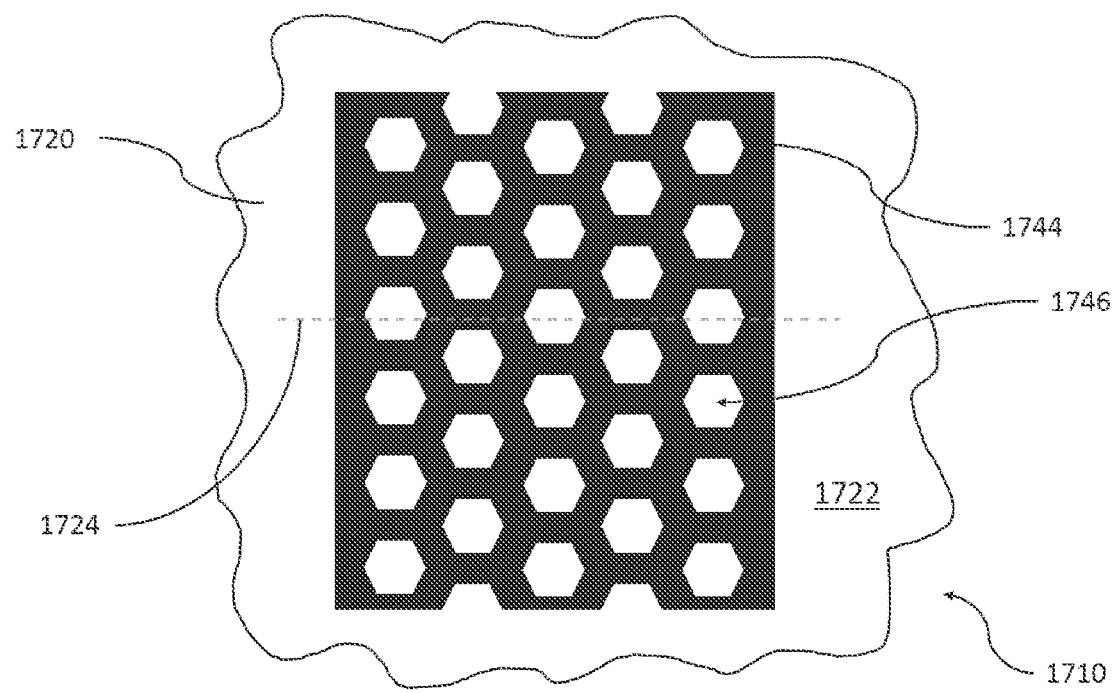
FIG. 26 is a detail view of a conductive material trace in an interconnecting pattern with a hexagonal grid.

FIG. 26 is the patterned interconnect 1744 with a hexagonal shape to the voids 1746. As a result, when the flexible base substrate 20 is bent along the axis of flexion 1724, the first base substrate layer 1721 and the patterned interconnect 1744 will bend along an axis that includes both the patterned interconnect 1744 and the voids 1746.

Figure 27:
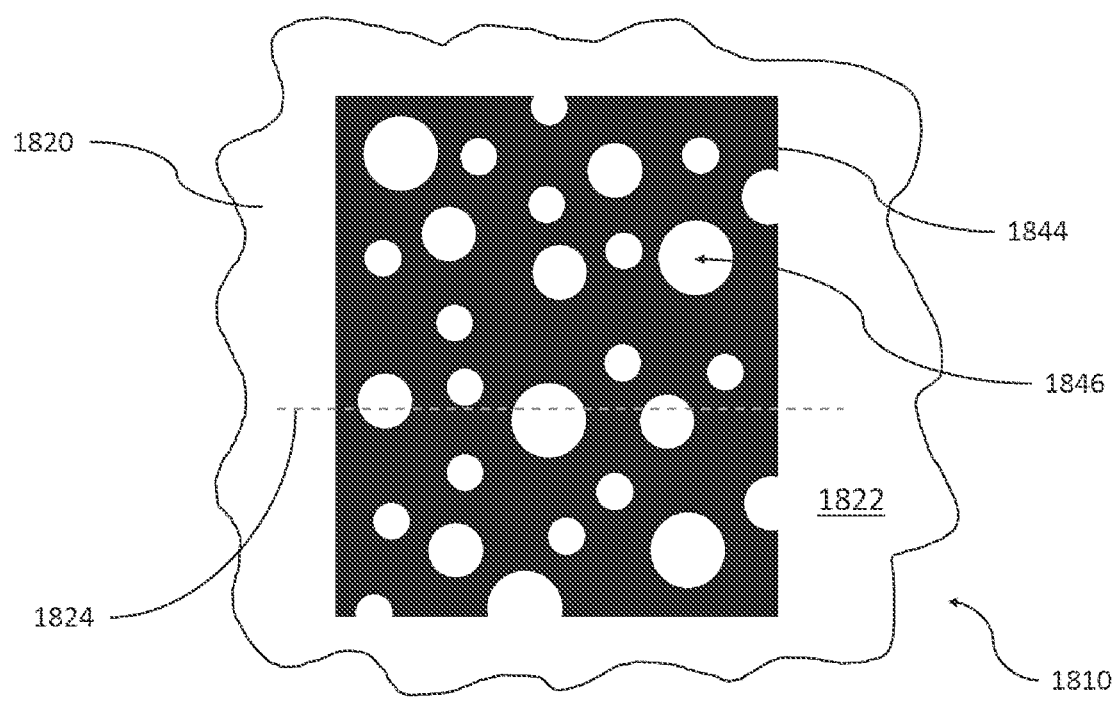
FIG. 27 is a detail view of a conductive material trace in an interconnecting pattern with offset circular voids.

FIG. 27 is the patterned interconnect 1844 with a circular shape to the voids 1846. As a result, when the flexible base substrate 20 is bent along the axis of flexion 1824, the first base substrate layer 1821 and the patterned interconnect 1844 will bend along an axis that includes both the patterned interconnect 1844 and the voids 1846.

In the preceding description, for purposes of explanation, numerous details are set forth in order to provide a thorough understanding of the embodiments. However, it will be apparent to one skilled in the art that these specific details are not required. In other instances, well-known electrical structures and circuits are shown in block diagram form in order not to obscure the understanding. For example, specific details are not provided as to whether the embodiments described herein are implemented as a software routine, hardware circuit, firmware, or a combination thereof.

Embodiments of the disclosure can be represented as a computer program product stored in a machine-readable medium (also referred to as a computer-readable medium, a processor-readable medium, or a computer usable medium having a computer-readable program code embodied therein). The machine-readable medium can be any suitable tangible, non-transitory medium, including magnetic, optical, or electrical storage medium including a diskette, compact disk read only memory (CD-ROM), memory device (volatile or non-volatile), or similar storage mechanism. The machine-readable medium can contain various sets of instructions, code sequences, configuration information, or other data, which, when executed, cause a processor to perform steps in a method according to an embodiment of the disclosure. Those of ordinary skill in the art will appreciate that other instructions and operations necessary to implement the described implementations can also be stored on the machine-readable medium. The instructions stored on the machine-readable medium can be executed by a processor or other suitable processing device, and can interface with circuitry to perform the described tasks.

The above-described embodiments are intended to be examples only. Alterations, modifications and variations can be effected to the particular embodiments by those of skill in the art. The scope of the claims should not be limited by the particular embodiments set forth herein, but should be construed in a manner consistent with the specification as a whole.

What is claimed is:

1. A method for mitigating propagation of a crack in a conductive material connected with a flexible base comprising:
   a. communicating data through the conductive material between a termination point connected with the flexible base, and an interface, the interface for communicating through a circuit package,
   wherein communicating the data through the conductive material comprises communicating the data through at least a first portion of the conductive material, the first portion of the conductive material comprising a first interconnect, the first interconnect comprising at least two leads, and the two leads separated by a void.

2. The method of claim 1 wherein the termination point comprises an input module for receiving the data and the interface comprises an output interface for providing the data externally to the circuit package.

3. The method of claim 2 wherein the input module comprises a sensor and the data comprises data of a stimulus on the sensor.

4. The method of claim 3 wherein the sensor comprises a force-sensitive area and the stimulus comprises application of a force to the force-sensitive area.

5. The method of claim 4 wherein:
   the force-sensitive area comprises:
   a first electrode connected with the flexible base, the first electrode comprising a first sensor portion in electrical communication with the conductive material; and
   a second electrode connected with the flexible base, the second electrode comprising a second sensor portion in electrical communication with the conductive material;
   wherein the first electrode is positioned relative to the second electrode to be in electrical isolation from the second electrode in the absence of the force and to be urged into contact with the second electrode when the force is applied to the force-sensitive area.

6. The method of claim 4, wherein the force-sensitive area comprises an electrode having an electrical property that is variable in response to the force.

7. The method of claim 5 wherein the force-sensitive area comprises a conductor bridge connected with the flexible base for providing electrical communication between the first electrode and the second electrode when the force is applied to the force-sensitive area.

8. The method of claim 7 wherein:
   The flexible base comprises a first base substrate layer connected with a second base substrate layer;
   the first electrode is connected with the first base substrate layer; the second electrode is connected with the first base substrate layer;
   the force-sensitive area comprises a conductor bridge connected with the second base substrate layer; and
   the conductor bridge is positioned on the second substrate layer relative to the first electrode and the second electrode for providing electrical communication between the first electrode and the second electrode when the force is applied to the force-sensitive area.

9. The method of claim 5 wherein the first portion of the conductive material extends between the first sensor portion and the output interface.

10. The method of claim 2 wherein:
    a second portion of the conductive material comprises a second interconnect including at least two leads of the conductive material, the two leads separated by a void; and
    the second portion of the conductive material extends between the second sensor portion and the output interface.

11. The method of claim 4 further comprising a fluid channel in communication with the force-sensitive area for relief of air pressure within the flexible base when the force-sensitive area is exposed to pressure.

12. The method of claim 1 further comprising an output module for changing state in response to a signal, and the interface comprises an input interface for providing a signal to the output module.

13. The method of claim 1 wherein the termination point comprises an output module for changing state in response to a signal, and the interface comprises an input interface for providing a signal to the output module.

14. The method of claim 3 wherein the termination point comprises an electrode having an electrical property that is variable in response to temperature and the stimulus comprises a change in temperature.

15. The method of claim 1 wherein the first interconnect comprises a plurality of leads of the conductive material separated by a plurality of voids for mitigating crack propagation through the conductive material.

16. The method of claim 15 wherein the plurality of leads of the conductive material are staggered relative to plurality of voids.

17. The method of claim 15 wherein the plurality of leads of the conductive material are positioned relative to the voids in an orthogonal grid, a non-orthogonal quadragonal grid, a hexagonal grid, offset voids or offset circular voids.

18. The method of claim 1 further comprising an expected axis of flexion.

19. The method of claim 18 wherein the first interconnect is located along the expected axis of flexion.

20. The method of claim 2 comprising a reinforcement element connected with the flexible base covering at least the surface area of the input module and a connection point between the termination point and the conductive material, the reinforcement element having a greater rigidity than the flexible base.

\* \* \* \* \*